United States Patent
Tayi et al.

(10) Patent No.: US 11,821,017 B2
(45) Date of Patent: Nov. 21, 2023

(54) METHODS TO PRODUCE SINGLE GLYCOFORM ANTIBODIES

(71) Applicant: The University of Manitoba, Winnipeg (CA)

(72) Inventors: Venkata Tayi, Winnipeg (CA); Michael Butler, Winnipeg (CA)

(73) Assignee: University of Manitoba, Winnipeg (CA)

( * ) Notice: Subject to any disclaimer, the term of this patent is extended or adjusted under 35 U.S.C. 154(b) by 1 day.

(21) Appl. No.: 16/736,654

(22) Filed: Jan. 7, 2020

(65) Prior Publication Data

US 2020/0255879 A1 Aug. 13, 2020

Related U.S. Application Data

(63) Continuation of application No. 15/118,664, filed as application No. PCT/CA2015/000093 on Feb. 18, 2015, now abandoned.

(Continued)

(51) Int. Cl.
| | |
|---|---|
| C12P 21/00 | (2006.01) |
| C07K 1/22 | (2006.01) |
| C07K 16/00 | (2006.01) |
| C12P 19/18 | (2006.01) |
| C07K 16/24 | (2006.01) |
| C07K 16/28 | (2006.01) |

(52) U.S. Cl.
CPC .............. *C12P 21/005* (2013.01); *C07K 1/22* (2013.01); *C07K 16/00* (2013.01); *C07K 16/244* (2013.01);

(Continued)

(58) Field of Classification Search
None
See application file for complete search history.

(56) References Cited

U.S. PATENT DOCUMENTS

2011/0263828 A1 10/2011 Wong
2013/0171658 A1* 7/2013 Fulton ................. C08B 37/0003
435/7.1

OTHER PUBLICATIONS

Warnock D, Bai X, Autote K, Gonzales J, Kinealy K, Yan B, Qian J, Stevenson T, Zopf D, Bayer RJ. In vitro galactosylation of human IgG at 1 kg scale using recombinant galactosyltransferase. Biotechnol Bioeng. Dec. 30, 2005;92(7):831-42. doi: 10.1002/bit.20658. PMID: 16187338. (Year: 2005).*

(Continued)

*Primary Examiner* — Michelle S Horning
(74) *Attorney, Agent, or Firm* — Michael R. Williams; Ryan W. Dupuis; Ade & Company Inc.

(57) ABSTRACT

An enzymatic method is provided for restructuring an affinity ligand bound heterogenous glycoform antibody sample to a substantially homogenous single desired glycoform antibody sample for therapeutic uses and kits for performing the methods. A method for enzymatically altering the Fc region of an affinity ligand bound antibody from a heterogenous glycoform to a substantially homogenous single glycoform comprises: contacting the affinity ligand bound heterogeneous glycoform antibody with a reaction buffer designed for a particular glycoform modification for a time sufficient and under conditions to modify the glycoform of the Fc region to a substantially homogeneous single form; optionally adding one or more nucleotide sugars and/or cofactors; and releasing the substantially homogeneous single glycoform antibody sample from said affinity ligand. The invention also encompasses biopharmaceuticals comprising single glycoform mAbs and polyclonal antibodies enzymatically produced for the treatment of cancers and immune disorders as well as compositions comprising the single glycoform antibodies as a biopharmaceutical.

19 Claims, 8 Drawing Sheets

Related U.S. Application Data

(60) Provisional application No. 61/941,172, filed on Feb. 18, 2014.

(52) U.S. Cl.
CPC .......... *C07K 16/2863* (2013.01); *C12P 19/18* (2013.01); *C07K 2317/24* (2013.01); *C07K 2317/41* (2013.01)

(56) References Cited

OTHER PUBLICATIONS

Robertson MW, Albrandt K, Keller D, Liu FT. Human IgE-binding protein: a soluble lectin exhibiting a highly conserved interspecies sequence and differential recognition of IgE glycoforms. Biochemistry. Sep. 4, 1990;29(35):8093-100. (Year: 1990).*

Chung, Seung-Wook et al., "Galactosylation and sialylation of terminal glycan residues of human immunoglobulin G using bacterial glycosyltransferases with in situ regeneration of sugar-nucleotides" Enzyme and Microbial Technology, 2006, pp. 60-66, vol. 39.

Hodoniczky, Jason et al., "Control of Recombinant Monoclonal Antibody Effector Functions by Fc N-Glycan Remodeling in Vitro" Biotechnol. Prog., 2005, pp. 1644-1652, vol. 21.

Yu, Marcella et al., "Production, characterization and pharmacokinetic properties of antibodies with N-linked Mannose-5 glycans" mAbs, Jul./Aug. 2012, pp. 475-487, vol. 4, No. 4.

International Search Report for PCT/CA2015/000093 dated May 19, 2015.

Supplementary European Search Report for EP 15752527 dated Oct. 12, 2017.

* cited by examiner

METHODS TO PRODUCE SINGLE GLYCOFORM ANTIBODIES

RELATED APPLICATIONS

This application is a Continuation of and claims the benefit and priority to U.S. patent application Ser. No. 15/118,664, filed on Aug. 12, 2016, which is a U.S. National Phase Application of PCT International Application Number PCT/CA2015/000093, filed on Feb. 18, 2015, designating the United States of America and published in the English language, which is an International Application of and claims the benefit of priority to U.S. Provisional Application No. 61/941,172, filed on Feb. 18, 2014. The disclosures of the above-referenced applications are hereby expressly incorporated by reference in their entireties.

FIELD OF THE INVENTION

The present invention relates to the production of antibodies with a desired glycosylation profile. More specifically, the invention provides enzymatic methods designed to produce a population of single glycoform mAbs for therapeutic uses and kits for performing the methods. The invention encompasses single glycoform polyclonal and monoclonal antibodies as biopharmaceuticals enzymatically produced for the treatment of cancers and immune disorders as well as biopharmaceutical compositions comprising the single glycoform antibodies.

BACKGROUND OF THE INVENTION

Antibodies, also known as immunoglobulins (Igs), play a critical role in our immune system. There are five major classes of Igs: IgG, IgA, IgD, IgM and IgE in the immune system. Among these, IgGs are most abundantly available antibodies in the immune system. The IgG antibody is composed of two light and two heavy chains that are associated with each other to form three major domains connected through a flexible hinge region: the two identical antigen-binding (Fab) regions and the constant (Fc) region. The Fc region is a homodimer in which the two identical fragments, each fragment consists of $C_H2$ and $C_H3$ domains, are paired through non-covalent interactions.

Monoclonal antibodies represent new pharmacological tools for the treatment of human diseases such as for cancer and for autoimmune diseases. In particular, all the approved monoclonal antibodies for therapy are of the IgG type. Recombinant monoclonal antibodies (mAbs) are designed by combining an engineered Fab fragment to target specific antigen with at least Fc fragment of native human IgG. These antibodies can be chimeric, humanized or fully human type. In some cases, the engineered Fab fragment can be monomer making it a heavy chain only monoclonal antibody. In some cases, the Fab fragment is replaced with a peptide making it a Fc-fusion protein.

Regardless of type, a common mechanism of action can be defined for all antibodies. The Fab region binds specifically to a target antigen on a cell surface or in extracellular environment, whereas the Fc fragment determines the mechanism in which the antibody works by binding to specific receptors. The most widely acceptable mechanisms of Fc-mediated effector functions are antibody-dependent cell-mediated cytotoxicity (ADCC) and complement-dependent cellular cytotoxicity (CDC). In ADCC, natural killer (NK) cell or neutrophil binds to Fc region of the antibody through its FcγRIIIa or FcγRIIa receptor, respectively, and react by secreting cell-lytic agents to lyse the target cell bound to Fab region. In CDC mechanism, the C1q component of complement complex binds to the Fc region of antibody and initiates a cascade of reactions to lyse the target cell. One of the suggested mechanisms of Igs in providing anti-inflammatory response for treating autoimmune or inflammatory diseases is by the increased expression of inhibitory FcγRIIb receptors on macrophages through cytokine signaling triggered by the binding of Fc to DC-SIGN receptors on dendric cells.

Glycosylation is a post-translational modification of proteins in which oligosaccharide structures are covalently attached to the protein. N-glycosylation is referred to the attachment of glycans to nitrogen of asparagine in a conserved amino acid sequence of protein (asn-xxx-ser/thr, where xxx is any amino acid except proline or aspartate). For IgGs, an N-glycan is present in the conserved CH2 domain of each Fc chain, results in a pair of glycans in Fc region. N-glycans can be present as high mannose, hybrid or complex structures with a common core consisting of 2 GlcNAc and 3 Mannose residues. The N-glycans most commonly associated with native IgGs and IgG-based mAbs are complex bi-antennary chains, predominantly with core fucose.

The structure of the N-glycans and the presence of a particular sugar as terminal residue play a critical role in modulating the pharmacokinetic properties and effector functions of antibodies. It is known that appropriate glycosylation at the conserved glycosylation site (N297) of the Fc domain is essential for the efficient interactions between mAbs and Fc receptors (FcR) and for the FcR-mediated effector functions, including antibody-dependent cell-mediated cytotoxicity (ADCC) and complement-dependent cytotoxicity (CDC). Different forms of glycosylation (i.e., glycosylation states) exert significantly different effects. Some are beneficial while others are detrimental. The different IgG-Fc glycosylation states have been shown to elicit significantly different effector functions.

The therapeutic efficacy and anti-inflammatory property of mAbs is greatly dependent on the oligosaccharide structure linked in the Fc region. For example, the absence of core fucose was found to enhance antibody-dependent cell-mediated cytotoxicity (ADCC) of mAb dramatically up to 50-fold [Shields, R. L., et al., *Lack of fucose on human IgG1 N-linked oligosaccharide improves binding to human Fcgamma RIII and antibody-dependent cellular toxicity*. J Biol Chem, 2002. 277(30): p. 26733-40]. Also, adding bisecting GlcNAc to inner core mannose reported to enhance the ADCC activity [Umana, P., Jean-Mairet, J., Moudry, R., Amstutz, H., Bailey, J. E., 1999. *Engineered Glycoforms of an Antineuroblastoma Igg1 with Optimized Antibody Dependent Cellular Cytotoxic Activity. Nature Biotechnology* 17, 176-180]. The presence of galactose as terminal sugar in N-glycans of IgGs seems to enhance their binding affinity to FcRIIIa receptors [Houde, D., Peng, Y., Berkowitz, S. A., Engen, J. R., 2010. *Post-Translational Modifications Differentially Affect IgG1 Conformation and Receptor Binding. Mol Cell Proteomics* 9, p. 1716-1728]. Highly galactosylated antibodies found to have higher ADCC activity for some cases [Kumpel, B. M., Rademacher, T. W., Rook, G. A. W., Williams, P. J., Wilson, I. B. H., 1994. *Galactosylation of Human IgG Monoclonal Anti-D Produced by Ebv-Transformed B-Lymphoblastoid Cell Lines Is Dependent on Culture Method and Affects Fc Receptor-Mediated Functional Activity. Human Antibodies and Hybridomas* 5, 143-151]. The absence of terminal galactose was found to reduce CDC activity of Campath®

[Boyd, P. N., Lines, A. C., Patel, A. K, 1995. *The Effect of the Removal of Sialic Acid, Galactose and Total Carbohydrate on the Functional Activity of Campath-1h. Molecular Immunology* 32, 1311-1318] and Rituxan® [Hodoniczky, J., Y. Z. Zheng, and D. C. James, *Control of Recombinant Monoclonal Antibody Effector Functions by Fc N-Glycan Remodeling in Vitro.* Biotechnol Prog, 2005. 21(6): p. 1644-1652.]. On the other hand, the antibodies with terminal sialic acid in N-glycans found to have reduced ADCC activity [Scallon, B. J., et al., *Higher levels of sialylated Fc glycans in immunoglobulin G molecules can adversely impact functionality.* Molecular Immunology, 2007. 44(7): p. 1524-1534] increased anti-inflamatory property [Kaneko, Y., F. Nimmerjahn, and J. V. Ravetch, *Anti-Inflammatory Activity of Immunoglobulin G Resulting from Fc Sialylation. Science,* 2006. 313(5787): p. 670-673].

Animal cells are the primary choice for expressing and producing recombinant mAbs because of their ability to link oligosaccharides to proteins. Glycosylation is a sequential process with series of enzymatic reactions and depends on various metabolic pathways. The complexity of glycosylation process and its dependency on the cellular metabolism result in the production of heterogeneous population of mAbs with various oligosaccharide structures. This is mainly due to inefficient processing of the glycans in Golgi during production. Also, batch to batch variability in glycosylation during production may also encounter due to alteration of metabolic state of cells. Recombinant mAbs are produced currently via genetic engineering, with the result that the antibody protein is present as a mixture of glycosylation states (also known as glycoforms of the mAb), in which the more active glycoform (e.g., galactosylated, de-fucosylated and/or bisecting GlcNAc-containing N-glycans) may be present only in minor amounts or as a component of 5 or more glycoforms. All currently marketed mAbs are available as a mixture of mAb glycoforms as a result of their genetic engineering origin.

Efforts have focused to engineer mAbs to optimize their therapeutic properties with respect to decreased immunogenicity, better avidity/affinity and optimized effector functions. One manner of optimizing is the alteration of mAbs glycosylation profiles. Cellular glycosylation engineering has emerged as an attractive approach to obtain human-like, homogeneous glycoproteins for structural studies and for biomedical applications, however, the cellular glycol-engineering approaches available still result in the production of heterogeneous mAbs having various glycosylation states. In addition, genetic engineering of an expressing system may result in instability and low expression efficiency of the host system.

Homogeneous glycoform antibodies are useful to investigate structural and functional abilities of the glycoforms which in turn provides opportunity to generate antibodies with greater therapeutic efficacy. The production of homogeneous glycoform antibodies as final product is advantageous for pharmaceutical industries with respect to the quality attribute of the product during the regulatory process. Glyco-engineering strategies may address the issue of late limiting additions of sugar by enhancing or silencing the expression of glycosyltransferases. These strategies are not easily adapted to established upstream production platforms. In addition, the processing of glycans may not be able to match up with the trafficking of product in the Golgi because of the developments in productivity enhancement up to 5 g/L.

Attempts have been made for in-vitro modification of glycans up to 1 Kg scale in solution [Warnock, D., Bai, X. M, Autote, K., Gonzales, Kinealy, K., Yan, B., Oian, J., Stevenson, T., Zopf, D., Bayer, R. J., 2005. *In Vitro Galactosylation of Human Igg at 1 Kg Scale Using Recombinant Galactosyltransferase. Biotechnology and Bioengineering* 92, p. 831-842]. However, this way of in-vitro modification requires several steps for processing and purification of antibodies from enzymes and buffers, especially when multiple modifications are required to reach desired glycoform. This results in product loss during each step and a high cost of downstream processing. U.S.2011/0263828 describes a method to modify the N-glycans of antibodies by glycan engineering. The method aims to modify the N-glycans by a complex multistep series of enzymatic processes.

U.S.2013/0217863 describes a method to produce recombinant antibodies that have an improved glycosylation profile via the use of nucleic acid sequences coding for a variant Fc region in order that the Fc region has a low fucose level and/or high oligomannose level and/or high level of sialylated glycoform.

U.S. 2013/0171658 describes a method to isolate and deglycosylate glycoproteins allowing for the quantification of the glycoprotein, such as an antibody, and for the analysis of glycans attached thereto. The method aimed to quantitatively recover the target glycoprotein and the glycan released from the protein.

There still remains a need to provide improved immunotherapy treatments that harness the specificity of the immune response. To come to such treatments there is required a method which can be used in a large scale to produce desired single glycoform mAbs that can be tailored to a specific clinical indication in order to provide a more effective immunotherapy with decreased immunogenicity, better avidity/affinity and optimized effector functions.

SUMMARY OF THE INVENTION

The present invention provides an efficient and effective method for in-vitro modification of antibodies to obtain a single glycoform population with desired glycosylation structure. The method of the invention provides for the downstream processing of antibodies with a heterogeneous glycoform profile to provide for a preselected single glycoform profile. In this manner the antibody structure is enzymatically modified in a single step so that it fits a single glycoform profile selected for a specific therapeutic application.

Simply stated, the method of the invention presents an immobilized heterogeneous population of antibodies, in aspects monoclonal antibodies, from a cell culture supernatant that are restructured/modified with the use of enzymes and/or nucleotide sugars and/or cofactors in a single step to provide a desired glycan profile for a certain therapeutic treatment.

Simply stated, in another embodiment, the method of the invention presents an immobilized heterogeneous population of antibodies, in aspects polyclonal antibodies, from a serum sample that are restructured/modified with the use of enzymes and/or nucleotide sugars and/or cofactors in a single step to provide a desired glycan profile for a certain therapeutic treatment.

In aspects, in the method a heterogeneous mAb sample is bound to an affinity ligand for enzymatic modification and subsequently released as a homogenous mAb sample with respect to glycosylation pattern of the Fc region. It was surprising and unexpected that an affinity ligand bound mAb could be effectively enzymatically modified as the N-glycans of the mAb was not previously thought to be accessible in a manner that would allow tailored enzymatic modification. The method of the invention can be easily integrated into an antibody purification process thereby providing a novel, efficient and cost-effective process of in vitro antibody glycan modification.

The method of the invention is desirous for several reasons: it is applicable to modify any heterogeneous glycoform monoclonal antibody sample without any modification to upstream production process: in vitro modification and purification can be performed in a single integrated step by selection of the enzyme(s): provides complete recovery of the product by reducing the number of downstream processing steps and thereby the cost: desired glycosylation pattern of the antibody can be changed based on the requirement without any significant changes to existing antibody producing cell lines: a final antibody product with single-glycoform structure can be produced for regulatory acceptance compared to a heterogeneous product: and the method of the invention is not limited to any single antibody type and in fact can be applied to wide range of antibodies, and in particular, monoclonal antibodies.

The method of the invention is useful to produce a desired single glycoform mAb targeted for a cancer therapy or for treatment of immune disorders and inflammatory disorders as is understood by one of skill in the art. As designed and made for the treatment of autoimmune disorders or inflammatory disorders, in aspects the presence of terminal sialic acid in the glycans of Fc region is desired. As designed and made for the treatment of cancer, the presence of terminal galactose in the glycans of Fc region is needed.

The invention encompasses therapeutic methods to treat cancers, autoimmune and inflammatory disorders with the single glycoform mAb so produced by the present invention. Such immunotherapy can be combined with other traditional methods of therapies and pharmaceuticals known and used in the treatment of cancers, autoimmune disorders and inflammatory disorders.

Aspects of the invention include the modification of representative but non-limiting monoclonal antibodies: EG2-hFc, Cetuximab and aIL8-hFc as well as polyclonal serum IgGs, that were modified as follows to produce a single glycoform: Conversion to G2 glycoform (with galactose as terminal sugar); Conversion to G0 glycoform (with GlcNAc as terminal sugar); Conversion to M3 glycoform (with mannose as terminal sugar); and Conversion to S2 glycoform (with sialic acid as terminal sugar) as herein described.

According to an aspect of the present invention is a method to enzymatically alter the Fc region of an affinity ligand bound antibody from a heterogeneous glycoform to a substantially homogenous single glycoform.

According to an aspect of the present invention is a method to enzymatically alter the Fc region of an affinity ligand bound antibody from a heterogeneous glycoform to a substantially homogenous single glycoform, the method comprising:
   (a) contacting said affinity ligand bound heterogeneous glycoform antibody with one or more enzymes for a time sufficient and under conditions to modify the glycoform of the Fc region to a substantially homogeneous single form;
   (b) optionally adding one or more nucleotide sugars and/or cofactors; and
   (c) releasing the substantially homogeneous single glycoform antibody sample from said affinity ligand.

In aspects, the antibody is a monoclonal antibody, and in still further aspects the antibody is an IgG monoclonal antibody. In other aspects the antibody is a polyclonal antibody, and further a polyclonal serum IgG.

In aspects the released substantially homogeneous single glycoform antibody sample is formulated into a biopharmaceutical.

According to an aspect of the invention is a biopharmaceutical isolated from the methods as described herein.

According to another aspect of the present invention is a method to enzymatically alter the Fc region of an antibody contained in a sample, from a heterogeneous glycoform to a substantially homogenous single glycoform, the method comprising:
   (a) adding the antibody sample to a solid phase support comprising an affinity ligand that binds said antibody in a manner that the glycans of the Fc region are exposed;
   (b) adding a reaction buffer comprising one or more enzymes for a time sufficient and under conditions to modify the glycoform of the Fc region to a first substantially homogeneous single form;
   (c) optionally adding one or more nucleotide sugars and/or cofactors;
   (d) optionally repeating step (b) one or more times with a further reaction buffer for a time sufficient and under conditions to modify the substantially homogeneous single glycoform to a second substantially homogeneous single glycoform; and
   (e) releasing the substantially homogeneous single glycoform antibody of step (b) or (d) from said affinity ligand.

In aspects, the antibody is a monoclonal antibody, and in still further aspects the antibody is an IgG monoclonal antibody.

According to an aspect of the present invention is an enzymatic method for modifying a heterogeneous glycoform mAb sample that is affinity bound to a substantially homogenous single glycoform mAb sample, the method comprising;
   (a) contacting said affinity ligand bound heterogeneous glycoform mAb sample with one or more enzymes for a time sufficient and under conditions to modify the glycoform to a single desired form;
   (b) optionally adding one or more nucleotide sugars and/or cofactors to (a); and
   (c) releasing the modified single glycoform mAb sample from said affinity ligand.

According to an aspect of the present invention is a method for the production of a substantially single glycoform mAb population from a heterogeneous glycoform mAb biological sample, said method comprising:
   (a) adding said biological sample to a solid phase support comprising an affinity ligand which binds to said target mAb to immobilize the mAb on said solid phase support;
   (b) washing said solid phase support with a buffer to wash away any unbound mAb and non-target proteins from said biological sample;
   (c) contacting said bound mAb on said solid phase support with one or more enzymes that that enzymatically alters glycans on said mAb to a desired single glycan profile;
   (d) optionally repeating step c) with additional enzymes to further alter the glycans to a different single glycan profile;
   (d) optionally adding one or more nucleotide sugars and/or cofactors to (c) and/or (d); and
   (e) eluting the single glycan profile mAb.

According to another aspect of the present invention is a method for the production of a biopharmaceutical that comprises a substantially single glycoform mAb population produced from a heterogeneous glycoform mAb biological sample, said method comprising:

(a) adding said biological sample to a solid phase support comprising an affinity ligand which binds and immobilizes said heterogeneous glycoform mAb on said solid phase support in a manner allowing for glycans of the Fc region exposure;

(b) contacting said bound heterogeneous glycoform mAb on said solid phase support with one or more enzymes that that enzymatically alters glycans in the Fc region to a desired glycan profile;

(c) optionally repeating step (b) to further alter the glycan profile obtained to a new single glycan profile;

(d) eluting the single glycan profile and providing as said biopharmaceutical useful for the treatment of cancers or immune disorders.

The method of the invention encompasses one or more washing steps after the affinity binding of the heterogeneous mAb on the support.

According to an aspect of the present invention is a method of generating mAbs having a desired single glycosylation profile in the Fc region for cancer immunotherapy; said method comprising:

(a) adding a heterogeneous mAb population to a solid phase support comprising an affinity ligand which binds to said heterogeneous mAb to immobilize the mAb on said solid phase support;

(b) washing said solid phase with a buffer to wash away any unbound mAb from said biological sample; and, (c) contacting said bound heterogeneous mAb population on said solid phase support with a reaction buffer comprising one or more enzymes to perform galactosylation and/or desialylation of said mAb; and (d) recovering a galactosylated and/or desialylated single glycoform mAb for cancer immunotherapy.

According to an aspect of the present invention is a method of generating mAbs having a desired single glycoform profile for immune disorder or inflammatory immunotherapy from a heterogeneous glycoform mAb population; said method comprising:

(a) adding said heterogeneous glycoform Ab population to a solid phase support comprising an affinity ligand which binds to said mAb to immobilize the mAb on said solid phase support;

(b) washing said solid phase with a buffer to wash away any unbound mAb from said biological sample; and, (c) contacting said bound mAb on said solid phase support with a reaction buffer comprising one or more enzymes to perform galactosylation and sialylation of said mAb at the Fc region; and (d) recovering the galactosylated and sialylated single glycoform mAb for immune disorder or inflammatory disorder immunotherapy.

In aspects of generating therapeutic mAbs for cancer, immune disorders or inflammatory immunotherapy, the step of washing may further wash away any unbound non-target proteins.

According to an aspect of the invention is a composition comprising mAb having a single glycoform for use in the treatment of a disorder. In aspects, the disorder is a cancer, autoimmune or inflammatory disorder.

According to an aspect of the invention is a biopharmaceutical mAb having a substantially single glycoform Fc region for use in the treatment of cancer, an autoimmune disorder or an inflammatory disorder.

According to an aspect of the invention is a biopharmaceutical mAb having a galactosylated substantially single glycoform Fc region for use in the treatment of cancer.

According to an aspect of the invention is a biopharmaceutical mAb having a sialylated substantially single glycoform Fc region for the treatment of an autoimmune disorder or an inflammatory disorder.

In aspects is a biopharmaceutical composition comprising a substantially homogeneous population of an antibody, wherein said antibody has an enzymatically modified glycoform on the Fc region, and said antibody is a monoclonal or polyclonal antibody. In aspects the modified glycoform is selected from the group consisting of G2 glycoform, G0 glycoform, M3 glycoform, S2 glycoform, A2B glycoform, A2BG2 glycoform and S1 glycoform. In aspects the monoclonal antibody is selected from EG2-hFc, Cetuximab and aIL8-hFc and said polyclonal antibody is human serum IgGs. In aspects the biopharmaceutical composition is for immunotherapy of a subject for the treatment of a condition selected from cancer, immune disorders or inflammatory disorders.

The invention is also directed to a method of treating a disorder in a subject comprising administering a biopharmaceutical comprising a single-glycoform mAb to the subject, wherein said single-glycoform mAb is designed for immunotherapy to treat a disorder selected from an autoimmune disorder, inflammation or cancer.

According to a further aspect of the invention is a kit for generating antibodies having a desired single-glycoform profile from a heterogeneous glycoform antibody population for immunotherapy; said kit comprising:

(a) a solid phase support comprising an affinity ligand which binds to a desired antibody to immobilize the antibody on said solid phase support;

(b) wash buffer;

(c) reaction buffer comprising one or more enzymes to perform a desired glycosylation profile of said antibody;

(d) optionally nucleotide sugar(s) and/or cofactor(s);

(e) optionally elution buffer and neutralization buffer; and (e) optional instructions for use.

The kit is suitable to produce monoclonal and/or polyclonal substantially homogenous glycoform as desired.

According to a further aspect of the present invention is a method to enzymatically alter the Fc region of an affinity ligand bound mAb from a heterogeneous glycoform to a substantially homogenous single glycoform, the method comprising:

(a) contacting said affinity ligand bound heterogeneous glycoform mAb with a reaction buffer designed to produce a single glycoform for a time sufficient and under conditions to modify the glycoform of the Fc region to a substantially homogeneous single form, where said single glycoform is selected from the group consisting of galactose as the terminal sugar, GlcNAc as the terminal sugar, mannose as the terminal sugar and sialic acid as the terminal sugar;

(b) adding one or more nucleotide sugars and/or cofactors; and (c) releasing the substantially homogeneous single glycoform antibody sample from said affinity ligand.

The foregoing has broadly outlined the features and technical advantages of the present invention in order that the detailed description of the invention that follows may be better understood. Additional features and advantages of the invention will be described hereinafter which form the subject of the claims of the invention. It should be appreciated by those skilled in the art that the specific embodiment disclosed herein may be readily utilized as a basis for modifying or designing other structures for carrying out the same purposes of the present invention. It should also be realized by those skilled in the art that such equivalent constructions do not depart from the scope of the invention. The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

DETAILED DESCRIPTION OF THE INVENTION

Figure 1:
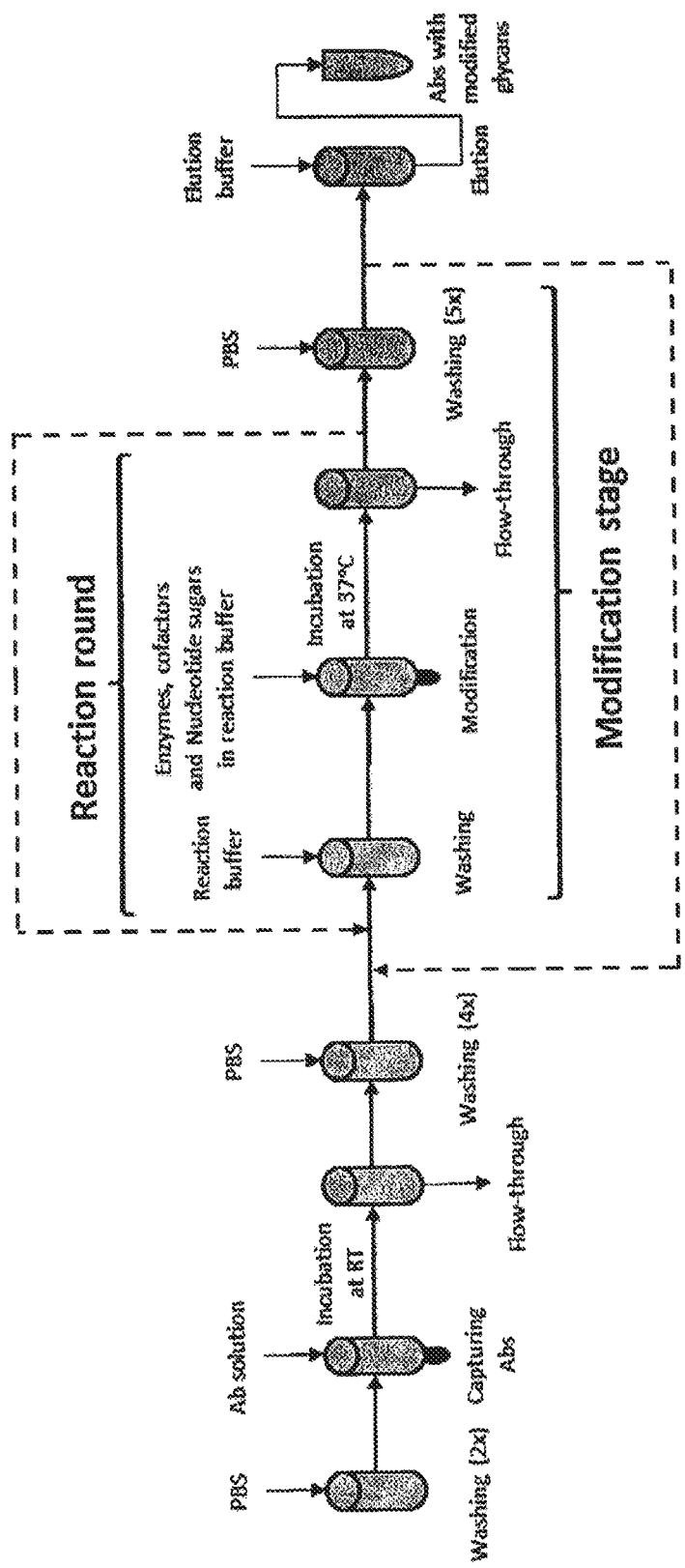
FIG. 1 shows a schematic representation of the steps involved in the in-vitro modification process. The dashed line represents the repetition of the steps, if needed, involved in that particular loop (i.e. reaction round is repeated to reach desired conversion yield or another modification stage is performed to convert from one glycoform to another. Reaction round may include reusing of enzymes from previous round by recycling it from inhibitory byproducts). The device consists of solid media (retained in the device) immobilized with affinity ligands to capture target antibodies.

The invention provides a fast and convenient method for the in vitro restructuring (conversion/modification) of antibodies to obtain single glycoform populations targeted for therapy of a preselected disease. In particular, the modification is to the Fc region of the antibody, in aspects a polyclonal and in other aspects, a monoclonal antibody. The method is suitable for integration into antibody purification processes for downstream antibody modification.

Surprisingly, the method is based on having the initial heterogeneous glycoform antibody bound in a manner that allows for modifying, purification and recovery of a designed modified single glycoform antibody in a single step. Modified single glycoform antibodies so produced can undergo further modification(s) as desired to produce any desired homogeneous antibody population for a therapeutic use. The method is both cost effective and applicable for a wide range of antibodies.

The method of the invention is applicable to a variety of sources of heterogeneous antibody populations such as but not limited to from cell culture supernatants and from serum (serum sources from a subject, such as a mammal, and in aspects, a human).

The method of the invention has particular use, in aspects, for the modification of monoclonal antibodies (mAbs). More specifically, the modification of the mAbs as taught herein relates to the Fc region of the antibody molecule, where the Fc region is modified to a single glycoform. The antibodies as used herein can be the antibody or any fragment thereof, including single chain, so long as it contains the Fc region. In embodiments this includes monoclonal antibodies, human monoclonal antibodies, humanized monoclonal antibodies and any recombinantly produced monoclonal antibodies.

Monoclonal antibodies produced and purified from a typical batch bioprocess consist of a heterogeneous mixture of glycoforms. The profile of these glycoforms is dependent upon various factors which include the array of enzyme activities present in the host cell as well as the culture conditions during the bioprocess. This heterogeneity in glycosylation is a disadvantage for various reasons. Firstly, it challenges the ability to obtain a consistent product from batch to batch. Secondly, it results in a mixture of glycoforms that would have variable functionality in therapeutic use. The desired functional role of the antibody may depend upon critical quality attributes of the antibody including its glycoform structure. For this reason there is a significant advantage in being able to produce a single glycoform antibody with a pre-determined structure.

The present invention obtains an essentially single glycoform by enzymatically restructuring the glycan following harvesting the antibody from a culture or serum. As the antibody is firmly bound to its affinity ligand its glycosylation can be restructured in a desired manner, and as such, the present method has the advantage that it can be easily incorporated into standard operating procedures used in antibody purification from culture supernatant or in aspects, from serum sources. Because the antibody is bound onto the solid matrix the quantity of enzymes required is significantly lower than would be the case in solution and the entire process can be achieved in a single step.

It is demonstrated herein the modifications can include complete galactosylation and sialylation by use of corresponding transferase enzymes and/or conversion to core non-galactosylated (G0) or core mannose (M3) structures or absence of core fucose.

Again, in the method of the invention, in one aspect is the enzymatic modification of glycans of the Fc region of a mAb antibody that is affected by immobilizing the antibodies to an affinity ligand in a manner that maintains the exposure of the glycans of the Fc region. Since affinity ligand purification of antibodies is performed as an initial step of purification after cell culture, this way of modification can be an easily integrated into that heterogenous process. The modification stage can be integrated into existing antibody purification processes. This results in a combined method of purification and modification as a single downstream processing step.

The accessibility of glycans in Fc region is important for in-vitro enzymatic modification. While glycans of antibodies in solution are accessible for in vitro modification, once bound to an affinity ligand, the accessibility cannot be predicted. The binding site of Protein-A is found to be a conserved region near the interface of $C_H2$-$C_H3$ domains of Fc [Deisenhofer, J., 1981. *Crystallographic Refinement and Atomic Models of a Human Fc Fragment and Its Complex with Fragment B of Protein a from Staphylococcus Aureus at 2.9-and 2.8-.Ang. Resolution. Biochemistry* 20, 2361-2370]. Protein A has high affinity towards human IgG1, IgG2 and IgG4. Protein G also binds at the same site as protein A [Stone, G. C., Sjobring, U., Bjorck, L., Sjoquist, J., Barber, C. V., Nardella, F. A., 1989. *The Fc Binding Site for Streptococcal Protein G Is in the C Gamma 2-C Gamma 3 Interface Region of Igg and Is Related to the Sites That Bind Staphylococcal Protein a and Human Rheumatoid Factors. Journal of immunology* (Baltimore, Md.: 1950) 143, 565-570], but has high affinity towards all human IgGs. However, whether the N-glycans of the antibody are accessible after its interaction with affinity ligand has not been studied and thus not before demonstrated. In the present invention, it is now demonstrated that N-glycans of antibodies are accessible for enzymatic modification after the antibody binds to the affinity ligand such as protein A, protein G and protein A/G fusion protein. Furthermore, it is also now presently demonstrated that enzymatic modification can be done in a manner that does not alter/reverse the binding during the process.

Definitions

Unless defined otherwise, all technical and scientific terms used herein generally have the same meaning as commonly understood by one of ordinary skill in the art to which this invention belongs. Generally, the nomenclature used herein and the laboratory procedures in cell culture, chemistry and immunology are those well-known and commonly employed in the art.

The articles "a" and "an" are used herein to refer to one or to more than one (i.e. to at least one) of the grammatical object of the article. By way of example, "an element" means one element or more than one element.

As used herein, "modify", "modification", "restructure", "remodel" with reference to the glycosylation are terms used synonymously.

As used herein, "antibody" refers to immune system-related proteins called immunoglobulins and their separately functional fragments. Each antibody consists of four polypeptides two heavy chains and two light chains joined to form a "Y" shaped molecule. Treating an antibody with a protease can cleave the protein to produce Fab or fragment antigen binding that include the variable ends of an antibody and/or the constant region fragment Fc. The constant region determines the mechanism used to destroy antigen (e.g. ADCC). Antibodies are divided into five major classes, IgM, IgG, IgA, IgD, and IgE, based on their constant region structure and immune function. These classes include subclasses such as $IgG_{1-4}$. An antibody may be polyclonal or monoclonal. (Harlow et al., 1999, Using Antibodies: A Laboratory Manual, Cold Spring Harbor Laboratory Press, NY; Harlow et al., 1989, Antibodies: A Laboratory Manual, Cold Spring Harbor, N.Y.; Houston et al., 1988, Proc. Natl. Acad. Sci. USA 85:5879-5883; Bird et al., 1988, Science 242:423-426).

"Antibody" (Ab) includes monoclonal antibodies, polyclonal antibodies, multispecific antibodies (e.g., bispecific antibodies), and antibody fragments that exhibit the desired biological activity. The term "immunoglobulin" (Ig) may be used interchangeably with "antibody".

An "antibody fragment" comprises a portion of an intact antibody, preferably the antigen binding or variable region of the intact antibody. Examples of antibody fragments include Fab, Fab', F(ab')2, and Fv fragments; linear antibodies (see U.S. Pat. No. 5,641,870; Zapata et al., Protein Eng. 8(10): 1057-1062 [1995]); single-chain antibody molecules; and multispecific antibodies formed from antibody fragments. For the purpose of the present invention, the antibody fragment is any kind described above but which also contains an Fc region.

The "Fc" fragment comprises the carboxy-terminal portions of both H chains held together by disulfides. The effector functions of antibodies are determined by sequences in the Fc region, which region is also the part recognized by Fc receptors (FcR) found on certain types of cells.

A "human antibody" as used herein refers to an antibody naturally existing in humans, a functional fragment thereof, or a humanized antibody, i.e., a genetically engineered antibody a portion of which (e.g., Fc region) derives from a naturally-occurring human antibody. A "humanized antibody" is generally considered to be a human antibody that has one or more amino acid residues introduced into it from a source that is non-human. These non-human amino acid residues are often referred to as "import" residues, which are typically taken from an "import" variable domain (Jones et al., Nature, 321:522-525 (1986); Reichmann et al., Nature, 332:323-327 (1988)), by substituting import hypervariable region sequences for the corresponding sequences of a human antibody. Accordingly, such "humanized" antibodies are chimeric antibodies wherein substantially less than an intact human variable domain has been substituted by the corresponding sequence from a non-human species. Furthermore, chimeric antibodies may comprise residues that are not found in the recipient antibody or in the donor antibody. These modifications are made to further refine antibody performance. For further details, see Jones et al., Nature 321:522-525 (1986); Riechmann et al., Nature 332:323-329 (1988); and Presta, Curr. Opin. Struct. Biol. 2:593-596 (1992).

As used herein, "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to polyclonal antibody preparations that include different antibodies directed against different determinants (epitopes), each monoclonal antibody is directed against a single determinant on the antigen. Monoclonal antibodies may be prepared by the hybridoma methodology (Kohler et al., Nature, 256:495 (1975)), or may be made using recombinant DNA methods in bacterial, eukaryotic animal or plant cells. Monoclonal antibodies may also be isolated from phage antibody libraries using the techniques described in Clackson et al., Nature, 352:624-628 (1991) and Marks et al., J. Mol. Biol., 222:581-597 (1991), for example.

"Synthetic antibody" as used herein, is meant an antibody which is generated using recombinant DNA technology, such as, for example, an antibody expressed by a bacteriophage as described herein. The term should also be construed to mean an antibody which has been generated by the synthesis of a DNA molecule encoding the antibody and which DNA molecule expresses an antibody protein, or an amino acid sequence specifying the antibody, wherein the DNA or amino acid sequence has been obtained using synthetic DNA or amino acid sequence technology which is available and well known in the art.

As used herein, the term "glycan" refers to a polysaccharide, or oligosaccharide. Glycan is also used herein to refer to the carbohydrate portion of a glycoconjugate, such as a glycoprotein, glycolipid, glycopeptide, glycoproteome, peptidoglycan, lipopolysaccharide or a proteoglycan. Glycans usually consist solely of β-glycosidic linkages between monosaccharides. Glycans can be homo or heteropolymers of monosaccharide residues, and can be linear or branched.

"N-linked" oligosaccharides are those oligosaccharides that are linked to a peptide backbone through asparagine, by way of an asparagine-N-acetylglucosamine linkage. N-linked oligosaccharides are also called "N-glycans." All N-linked oligosaccharides have a common pentasaccharide core of $Man_3GlcNAc_2$. They differ in the presence of, and in the number of branches (also called antennae) of peripheral sugars such as N-acetylglucosamine, galactose, N-acetylgalactosamine, fucose and sialic acid. Optionally, this structure may also contain a core fucose molecule and/or a xylose molecule.

"O-linked" oligosaccharides are those oligosaccharides that are linked to a peptide backbone through threonine or serine.

All oligosaccharides described herein are described with the name or abbreviation for the non-reducing saccharide (i.e., Gal), followed by the configuration of the glycosidic bond (α or β), the ring bond (1 or 2), the ring position of the reducing saccharide involved in the bond (2, 3, 4, 6 or 8), and then the name or abbreviation of the reducing saccharide (i.e., GlcNAc). Each saccharide is preferably a pyranose. For a review of standard glycobiology nomenclatures see, Essentials of Glycobiology Varki et al. eds., 1999, CSHL Press.

The term "sialic acid" refers to any member of a family of nine-carbon carboxylated sugars. The most common member of the sialic acid family is N-acetyl-neuraminic acid (2-keto-5-acetamido-3,5-dideoxy-D-glycero-D-galactononulopyranos-1-onic acid (often abbreviated as Neu5Ac, NeuAc, or NANA). A second member of the family is N-glycolyl-neuraminic acid (Neu5Gc or NeuGc), in which the N-acetyl group of NeuAc is hydroxylated. A third sialic acid family member is 2-keto-3-deoxy-nonulosonic acid (KDN) (Nadano et al. (1986) J. Biol. Chem. 261: 11550-11557; Kanamori et al., J. Biol. Chem. 265: 21811-21819 (1990)). Also included are 9-substituted sialic acids such as a 9-O—$C_1$-$C_6$ acyl-NeuSAc like 9-O-lactyl-Neu5Ac or 9-O-acetyl-NeuSAc, 9-deoxy-9-fluoro-Neu5Ac and 9-azido-9-deoxy-Neu5Ac. For review of the sialic acid family, see, e.g., Varki, Glycobiology 2: 25-40 (1992); Sialic Acids: Chemistry, Metabolism and Function, R. Schauer, Ed. (Springer-Verlag, New York (1992)). The synthesis and use of sialic acid compounds in a sialylation procedure is disclosed in WO 92/16640, the disclosure of which is incorporated herein in its entirety.

The term "exoglycosidase" used herein refers to an enzyme capable of hydrolysis of glycan structure from the out most non-reducing end. Examples of suitable exoglycosidase include, but are not limited to sialidase or neuraminidase, beta-galactosidase, alpha-fucosidase, and alpha-mannosidase.

The term "glycosyltransferase" used herein refers to an enzyme capable of transferring the monosaccharide moiety from a nucleotide sugar to an acceptor molecule such as a sugar molecule in an oligosaccharide. Examples of such glycosyltransferase include, but not limited to galactosyltransferase and sialyltransferase.

As used herein, "cancer" refers to a pathophysiological state whereby a cell is characterized by dysregulated and proliferative cellular growth and the ability to induce said growth, either by direct growth into adjacent tissue through invasion or by growth at distal sites through metastatsis in both, adults or children, and both acute or chronic, including, but not limited to, carcinomas and sarcomas, such as, acute lymphoblastic leukemia, acute myeloid leukemia, adrenocortical cancer, AIDS-related cancers, AIDS-related lymphoma, anal cancer, astrocytoma (cerebellar or cerebral), basal cell carcinoma, bile duct cancer, bladder cancer, bone cancer, brain stem glioma, brain tumor (e.g., ependymoma, medulloblastoma, supratentorial primitive neuroectodermal, visual pathway and hypothalamic glioma), cerebral astrocytoma/malignant glioma, breast cancer, bronchial adenomas/carcinoids, Burkitt's lymphoma, carcinoid tumor (e.g., gastrointestinal), carcinoma of unknown primary site, central nervous system lymphoma, cervical cancer, chronic lymphocytic leukemia, chronic myelogenous leukemia, chronic myeloproliferative disorders, colon cancer, colorectal cancer, cutaneous T-Cell lymphoma, endometrial cancer, ependymoma, esophageal cancer, Ewing's Family of tumors, extrahepatic bile duct cancer, eye cancer (e.g., intraocular melanoma, retinoblastoma, gallbladder cancer, gastric cancer, gastrointestinal carcinoid tumor, gastrointestinal stromal tumor (GIST), germ cell tumor (e.g., extracranial, extragonadal, ovarian), gestational trophoblastic tumor, glioma, hairy cell leukemia, head and neck cancer, squamous cell head and neck cancer, hepatocellular cancer, Hodgkin's lymphoma, hypopharyngeal cancer, islet cell carcinoma (e.g., endocrine pancreas), Kaposi's sarcoma, laryngeal cancer, leukemia, lip and oral cavity cancer, liver cancer, lung cancer (e.g., non-small cell), lymphoma, macroglobulinemia, malignant fibrous histiocytoma of bone/osteosarcoma, medulloblastoma, melanoma, Merkel cell carcinoma, mesothelioma, metastatic squamous neck cancer with occult primary, mouth cancer, multiple endocrine neoplasia syndrome, multiple myeloma/plasma cell neoplasm, mycosis fungoides, myelodysplastic syndromes, myelodysplastic/myeloproliferative diseases, myeloma, nasal cavity and paranasal sinus cancer, nasopharyngeal cancer, neuroblastoma, non-Hodgkin's lymphoma, oral cancer, oral cavity cancer, osteosarcoma, oropharyngeal cancer, ovarian cancer (e.g., ovarian epithelial cancer, germ cell tumor), ovarian low malignant potential tumor, pancreatic cancer, paranasal sinus and nasal cavity cancer, parathyroid cancer, penile cancer, pharyngeal cancer, pheochromocytoma, pineoblastoma and supratentorial primitive neuroectodermal tumors, pituitary tumor, plasma cell neoplasm/multiple myeloma, pleuropulmonary blastoma, pregnancy and breast cancer, primary central nervous system lymphoma, prostate cancer, rectal cancer, retinoblastoma, rhabdomyosarcoma, salivary gland cancer, soft tissue sarcoma, uterine sarcoma, Sezary syndrome, skin cancer (e.g., non-melanoma or melanoma), small intestine cancer, supratentorial primitive neuroectodermal tumors, T-Cell Lymphoma, testicular cancer, throat cancer, thymoma and thymic carcinoma, thyroid cancer, transitional cell cancer of the renal pelvis and ureter, trophoblastic tumor (e.g. gestational), unusual cancers of childhood and adulthood, urethral cancer, endometrial uterine cancer, uterine sarcoma, vaginal cancer, vulvar cancer, Waldenstrom's macroglobulinemia and Wilms' Tumor.

As used herein, "immune-related disease or disorder" refers to a disease or disorder wherein the immune system is enhanced or suppressed or in which a component of the immune system causes, mediates, or otherwise contributes to morbidity or morality. Also included are diseases in which stimulation or intervention of the immune response has an ameliorative effect on progression of the disease or disorder. Included within this term are immune-mediated inflammatory diseases, non-immune-mediated inflammatory diseases, infectious diseases, immunodeficiency diseases, cancer, etc., including, for example, systemic lupus erythematosis, amyotrophic lateral sclerosis, Parkinson's disease, Alzheimer's disease, rheumatoid arthritis, juvenile chronic arthritis, spondyloarthropathies, systemic sclerosis (e.g., scleroderma), idiopathic inflammatory myopathies (e.g., dermatomyositis, polymyositis), Sjogren's syndrome, sarcoidosis, autoimmune hemolytic anemia (e.g., immune pancytopenia, paroxysmal nocturnal hemoglobinuria), autoimmune thrombocytopenia (e.g., idiopathic thrombocytopenic purpura, immune-mediated thrombocytopenia, thrombotic thrombocytopenic purpura), thyroiditis (e.g., Grave's disease, Hashimoto's thyroiditis, juvenile lymphocytic thyroiditis, atrophic thyroiditis), diabetes mellitus, immune-mediated renal disease (e.g., glomerulonephritis, tubulointerstitial nephritis), demyelinating diseases of the central and peripheral nervous systems (e.g., multiple sclerosis), idiopathic demyelinating polyneuropathy or Guillain-Barre syndrome, multiple myositis, mixed connective tissue disease, hyperthyroidism, myasthenia gravis, autoimmune hepatopathy, autoimmune nephropathy, vasculitidies (e.g. Kawasaki's disease or temporal arteriies), autoimmune hematopathy, idiopathic interstitial pneumonia, hypersensitivity pneumonitis, autoimmune dermatosis, autoimmune cardiopathy, cardiomyositis, autoimmune infertility, Behcet's disease, chronic inflammatory demyelinating polyneuropathy, hepatobiliary diseases (e.g., infectious hepatitis and other non-hepatotropic viruses), autoimmune chronic active hepatitis, primary biliary cirrhosis, granulomatous hepatitis, and sclerosing cholangitis, inflammatory bowel disease (e.g., ulcerative colitis: Crohn's disease), gluten-sensitive enteropathy, Whipple's disease, autoimmune or immune-mediated skin diseases including bullous skin diseases, vitiligo, erythema multiforme and contact dermatitis, psoriasis, sexually transmitted diseases, allergic diseases such as asthma, allergic rhinitis, atopic dermatitis, food hypersensitivity and urticaria, immunologic diseases of the lung such as eosinophilic pneumonias, idiopathic pulmonary fibrosis and hypersensitivity pneumonitis, transplantation associated diseases including graft rejection and graft-versus-host-disease, viral diseases (e.g., AIDS (HIV infection), hepatitis A, B, C, D, and E, herpes), bacterial infections, fungal infections, protozoal infections and parasitic infections.

As used herein, "inflammatory disorders" include and may overlap with some of the immune disorders listed above but also include autoimmune diseases, for example such as multiple sclerosis; vascular disorders including stroke, coronary artery diseases, myocardial infarction, unstable angina pectoris, atherosclerosis or vasculitis, e.g., Behcet's syndrome, giant cell arteritis, polymyalgia rheumatica, Wegener's granulomatosis, Churg-Strauss syndrome vasculitis, Henoch-Schonlein purpura and Kawasaki disease; viral infection or replication, e.g. infections due to or replication of viruses including pox virus, herpes virus (e.g., Herpesvirus saimiri), cytomegalovirus (CMV) or lentivirus; asthma; osteoporosis; (low bone mineral density); tumor growth; rheumatoid arthritis; organ transplant rejection and/or delayed graft or organ function, e.g. in renal transplant patients; a disorder characterised by an elevated TNF-α level; psoriasis; skin wounds; disorders caused by intracellular parasites such as malaria or tuberculosis; allergies; or Alzheimer's disease.

As used herein, with respect to antibodies, "substantially" means the desired product having a single glycosylation state, whether or not this state includes glycosylation at a single site or multiple sites. Typically, the antibody is substantially pure when it constitutes at least 60%, by weight, of the antibody in the preparation. For example, the antibody in the preparation is at least about 75%, in certain embodiments at least about 80%, in certain embodiments at about 85%, in certain embodiments at least about 90%, in certain embodiments at least about 95%, 96%, 97%, 98% and most preferably at least about 99%, by weight, of the desired antibody.

As used herein, "glycosylation state" refers to an antibody having a specific or desired glycosylation pattern. A "glycoform" is an antibody comprising a particular glycosylation state. Such glycosylation patterns include, for example, attaching one or more sugars at position N-297 of a mAb, wherein said sugars are produced naturally, recombinantly, synthetically, or semi-synthetically. The glycosylation pattern can be determined by many methods known in the art, see examples section. For example, methods of analyzing carbohydrates on proteins have been described in U.S. Patent Applications US 2006/0057638 and US 2006/0127950 (the disclosures of which are hereby incorporated by reference in their entirety).

The term "treating" and "treatment" as used herein refers to administering to a subject a therapeutically effective amount of an antibody so that the subject has an improvement in a disease. The improvement is any improvement or remediation of the symptoms. The improvement is an observable or measurable improvement. Thus, one of skill in the art realizes that a treatment may improve the disease condition, but may not be a complete cure for the disease. Specifically, improvements in patients with cancer may include tumor stabilization, tumor shrinkage, increased time to progression, increased survival or improvements in the quality of life. Improvements in patients with autoimmune disease may include improvement in laboratory values of inflammation, improvements in blood counts, improvements in rash, or improvements in the quality of life.

The term "therapeutically effective amount" as used herein refers to an amount that results in an improvement or remediation of the symptoms of the disease or condition.

The term "subject" as used herein, is taken to mean any mammalian subject to which an antibody composition is administered according to the methods described herein. In a specific embodiment, the methods of the present invention are employed to treat a human subject. Another embodiment includes treating a human subject suffering from cancer.

The term "biopharmaceutical" as used herein, is taken to mean the substantially single glycoform mAbs and polyclonal antibodies as produced by the method described herein.

Such a biopharmaceutical can be provided as a therapeutic composition further comprising suitable carriers and/or diluents as described herein.

Methods of the Invention

The present invention demonstrates that antibodies, irrespective of type and size, can be modified to single homogeneous glycoforms. More specifically, the glycosylation of the Fc regions can be tailored to specific therapeutic applications as desired. In embodiments, galactosylation of the Fc region of the antibody is useful for the treatment of cancers. In other embodiments, are provided methods for sialylation of the Fc region of an antibody to produce single glycoform antibodies for the treatment of autoimmune disorders. In other embodiments de-galactosylation may be desired and/or de-sialylation of the Fc region. Still in other embodiments production of hybrid structures having a core of GlcNAc and mannose residues may be effected such as N-Acetylglucosamine, GlcNAc; or mannose-N-Acetylglucosamine-N-Acetylglucosamine, Man-GlcNAc-GlcNAc. Any of the foregoing may be produced using the method of the invention, as any antibody can be modified in one step that may be repeated in a series in order to produce a desired single glycoform antibody population using the method of the invention.

G2 glycoforms in aspects were produced from a heterogeneous population of mAbs using the methods of the invention. The same method can be used to convert non-fucosylated heterogeneous population of antibodies, which can be produced by glyco-engineering methods, to homogeneous G2-glycoforms. In addition, the batch to batch variability of galactosylation of antibodies can also be addressed by modulating the galactosylation to desired level as per regulatory needs.

Referring to FIG. 1, briefly, the method of the invention encompasses applying an antibody population having a heterogeneous glycosylation state to a non-glycosylated affinity protein immobilized to a solid support. The antibody population can be from cell sources or from serum. In this representative example, the heterogeneous antibody population for modification is a mAb population. The support comprises a column that is washed with wash buffer and then with a second reaction buffer that is optimized for a corresponding desired modification. The second reaction buffer is optimized with the addition of selected enzyme(s), optionally cofactor(s) and optionally nucleotide sugar(s). The column is then incubated at 37° C. for up to about 48 hours with shaking, or in aspects up to about 72 hours. The columns are then washed again with the wash buffer that comprises a phosphate buffer and the modified single glycoform mAb is then eluted from the solid support using an elution buffer. The eluted single glycoform mAb may then neutralized using a neutralization buffer.

The nucleotide sugars for use in the reaction buffer are selected from the group consisting of UDP-Glc, UDP-Gal, UDP-GalNAc, UDP-GlcNAc, UDP-GlcUA, UDP-Xyl, GDP-Man, GDP-Fuc, CMP-Neu5Ac, CMP-Neu5Gc and combinations thereof. Concentrations used in the reaction buffer are in the range of about 0.5 to about 5 mM, in aspects from about 1 to about 1.5 mM. The cofactor for use in the reaction buffer may be selected from the group consisting of $Mn^{2+}$, $Ca^{+2}$, $Mg^{2+}$, $Na^+$, $K^+$, α-Lactalbumin and combinations thereof. Concentrations of cofactor for use in the reaction buffer may be in the range of about 2 to about 10 mM.

Processes for production of mAbs in mammalian cells results in a population with mixed glycosylation states, thus a heterogeneous mAbs population. In the method of the invention any desired mAb population can be used to create a single glycoform population by altering the glycan at the Fc region. In aspects, the antibody is a mAb, preferably an IgG antibody, and in certain embodiments IgG1 antibody. Non-exemplary antibodies contemplated include a therapeutic glycosylation-engineered antibody wherein the starting antibody includes, but is not limited to, cetuximab, rituximab, muromonab-CD3, abciximab, daclizumab, basiliximab, palivizumab, infliximab, trastuzumab, gemtuzumab ozogamicin, alemtuzumab, ibritumomab tiuxetan, adalimumab, omalizumab, tositumomab, 1-131 tositumomab, efalizumab, bevacizumab, panitumumab, pertuzumab, natalizumab, etanercept, IGN101 (APHTON™), volociximab (BIOGEN IDEC™ and PDL BIOPHARM™), Anti-CD80 mAb (BIOGEN IDEC™), Anti-CD23 mAb (BIOGEN IDEC™), CAT-3888 (CAMBRIDGE ANTIBODY TECHNOLOGY™), CDP-791 (IMCLONE™), eraptuzumab (IMMUNOMEDICS™), MDX-010 (MEDAREX™ and BMS™), MDX-060 (MEDAREX™), MDX-070 (MEDAREX™), matuzumab (MERCK™), CP-675,206 (PFIZER™), CAL (ROCHE™), SGN-30 (SEATTLE GENETICS™), zanolimumab (SERONO™ and GENMAB™), adecatumumab (SERONON™), oregovomab (UNITED THERAPEUTICS™), nimotuzumab (YM BIOSCIENCE™), ABT-874 (ABBOTT LABORATORIES™), denosumab (AMGEN™), AM 108 (AMGEN™), AMG 714 (AMGEN™), fontolizumab (BIOGEN IDEC™ and PDL BIOPHARM™), daclizumab (BIOGENT IDEC™ and PDL BIOPHARM™), golimumab (CENTOCOR™ and SCHERING-PLOUGH™), CNTO 1275 (CENTOCOR™), ocrelizumab (GENETECH™ and ROCHE™), HuMax-CD20 (GENMAB™), belimumab (HGS™ and GSK™), epratuzumab (IMMUNOMEDICS™), MLN1202 (MILLENIUM PHARMACEUTICALS™), visilizumab (PDL BIOPHARM™), tocilizumab (ROCHE™), ocrerlizumab (ROCHE™), certolizumab pegol (UCB™, formerly CELLTECH™), eculizumab (ALEXION PHARMACEUTICALS™), pexelizumab (ALEXION PHARMACEUTICALS™ and PROCTER & GAMBLE™), abciximab (CENTOCOR™), ranibizimumab (GENETECH™), mepolizumab (GSK™), TNX-355 (TANOX™), or MYO-029 (WYETH™). The mAb is provided as a sample and can be part of any conventional mAb processing system.

As is understood by one of skill in the art, any commercially available antibody can be modified as desired in the Fc region using the method of the invention. Furthermore, any newly synthesized antibody may be characterized with respect to its glycosylation pattern using methods known in the art and described for example in the Examples section provided herein. Any such any novel antibody (monoclonal and polyclonal) can be modified in its Fc region to produce a single glycoform population. Again, humanized, chimeric, single chain, fragments and the like as described herein containing a Fc region can be modified in accordance with the method of the invention. In desired aspects, the antibody is an IgG of any subclass comprising a Fc region due to its versatility in therapeutic applications. Antibody fragments can be readily produced via proteolytic digestion of intact antibodies or using recombinant techniques as is understood by one of skill in the art.

The method of the invention encompasses affinity chromatography using a solid support to isolate the mAb that is then enzymatically modified in a single step as it is bound to the support. Affinity chromatography columns are known to those of skill in the art incorporating a column or other type of solid support. The method may employ a variety of conventional solid phase extraction devices, such as small chromatography columns, spin columns, or pipette tips. The column is typically packed with a solid or stationary phase or medium (which may collectively be referred to as the "solid phase"), as is done for conventional affinity chromatography.

The solid phase comprises a molecule chosen for its specific biological interaction with the target mAb and is referred to herein as the "affinity ligand." Any ligand that has affinity towards antibodies can be used for these methods. Affinity ligands for use in the method of the invention include Protein A, a surface protein from the cell wall of Staphylococcus bacterium and Protein G, a cell surface protein from Streptococcus bacterium. Such ligands that have affinity for immunoglobulins include but not limited to: Protein A (native, recombinant), Protein G (native, recombinant and synthetic), Protein A-G fusion protein, Protein L. These are available from various commercial sources including but not limited to SIGMA-ALDRICH™ and REPLIGEN™. Some antibody fragments, sometimes referred to as VHHs, can also be used as affinity ligands for Immunoglobulins or antibodies. One commercial source of such antibody fragments is BAC BV (NAARDEN™, Netherlands).

The affinity ligands have to be immobilized on to solid media that is retained in the device during purification and modification process. The solid media include but not limited to agarose, sepharose, polyacrylic, polystyrine and other synthetic polymers which provide negligible non-specific adsorption of non-target proteins and enzymes of modification. The affinity ligand is covalently linked to the solid support by, for example any of a variety of chemistries, such as N-Hydroxysuccinimide (NHS) esters, epoxide, aldehyde, or cyanogen bromide, to a solid phase. Such conjugation chemistries are well-known in the art, as exemplified in Hermanson, G. T., Bioconjugate Techniques, Academic Press (Amsterdam, the Netherlands, Ed. 2008) and Wong, S., Chemistry of Protein Conjugation and Cross-Linking, CRC Press (Boca Raton, Fla., 1991).

The immobilized forms of protein A, Protein G, Protein A-G, Protein L and antibody fragments to agarose or sepharose or other matrices are commercially available from various sources. including but not limited to SIGMA-ALDRICH™, THERMOFISHER SCIENTIFIC™ and GE HEALTHCARE™, for capturing and purifying antibodies. The devices for the modification can be easily designed using commercially available empty columns for affinity chromatography depending on the scale of the product needed. The buffer exchanges in these columns can be done by either gravity flow or centrifugation or by pump. Such empty columns are commercially available from various sources including but not limited to THERMOFISHER SCIENTIFIC™ and BIORAD™.

In embodiments of the method of the invention, the columns utilized are microspin columns with immobilized protein A which has strong affinity towards immunoglobulin proteins. The optimization of buffer and incubation conditions is important to obtain desired result to perform the modifications. The column with immobilized affinity ligand is washed with a wash buffer prior to the loading with the selected mAb solution containing the heterogeneous population of mAbs with various Fc region glycan structures. After a period of incubation the column is again washed prior to the application of an optimized reaction buffer that contains the reactant mixture (one or more of enzymes, cofactors and nucleotide sugars). After a further period of incubation at temperatures of about 25° C. to about 40° C., in aspects about 37° C., the column is once again washed with the wash buffer and then elution buffer is applied that releases the modified mAb with desired glycosylation. An optional neutralization buffer as is understood by one of skill in the art can then be used to obtain a final pH of about 7.2.

The wash buffer is designed to maintain high affinity between antibodies and affinity ligands during washings. PBS with pH of about 7.2 can be used as wash buffer, however it is understood by one of skill in the art that the pH may vary to some degree. The wash and reaction buffers are designed to maintain high affinity between antibodies and affinity ligands and, at the same time, retain the activity of reaction enzymes. The wash and reaction buffers are used at temperatures of about 25° C. to about 40° C., and any temperature therein between. Temperatures of about 37° C. are often used. The optimum pH range for high affinity of antibodies to protein A, protein G and protein A/G is about 6.0 to about 8.0. Within this range of pH, the buffers overlap with optimum pH ranges of the affinity ligands can be used in the method of the invention. These include but are not limited to TRIS buffer, BIS-TRIS buffer, MES buffer, BES buffer, MOPS buffer and HEPES buffer.

Washing conditions for the affinity column minimizes non-specific binding and thus negatively affect enzyme reaction and thus mAb modification. Wash conditions are such that they will not break the bind between the affinity ligand and the target mAb.

Enzymes suitable for use in the methods of the invention are selected depending on the application for in vitro modification of antibodies using this method. These enzymes include but not limited to: Mannosyl-glucosamine transferases (MGAT1, MGAT2 and MGAT3); Galactosyltransferases (β4GalT1, β4GalT2, β4GalT3, β4GalT4, β4GalT5, β4GalT6, β4GalT7), Sialyltransferases (ST6Gal 1, ST6Gal2); Mannosidases (α Mannosidase-I, α Mannosidase-II, α(1-2) Mannosidase, α(1-6) Mannosidase, α(1-2,3) Mannosidase, α(1-2,3,6) Mannosidase); Hexosaminidases (β-N-acetylhexosaminidase, β-N-Acetylglucosaminidase, α-N-Acetylglucosaminidase); Galactosidases (β-galactosidase, β(1-4) galactosidase, α(1-3,6) galactosidase); Sialidases (α(2-3,6,8) sialidase, α(2-3) sialidase), fucosidases (α-L-Fucosidase, α(1-6) fucosidase, α(1-2) fucosidase, α(1-3,4) fucosidase, α(1-2,3,4) fucosidase) and any combinations thereof.

In representative but non-limiting embodiments of the invention, the method of the invention can be used to remove the terminal sialic acid from galactose for the antibodies aiming to target cancer. A terminal galactose is required in the glycans of the Fc region for cancer therapeutics. In one aspect, nonspecific neuraminidase enzyme is utilized which removes the sialic acid from any linkage. This enzyme was used in combination with galactosyltransferse to perform both galactosylation and removal of sialic acid in one single stage. This allowed for the generation of homogeneous G2 glycoform antibodies from a heterogeneous population of antibodies containing G0, G1, G2, S1 and S2 fractions.

In non-limiting representative aspects of the invention three monoclonal antibodies: EG2-hFc, Cetuximab and aIL8-hFc and polyclonal serum IgGs were used. These antibodies were modified as follows:

In one non-limiting embodiment: Conversion to G2 glycoform antibodies (FIGS. 3b, 4b, 5b and 9b);

In a further non-limiting embodiment: Conversion to G0 glycoform antibodies (FIGS. 3c, 4c, 5c and 9c);

In a further non-limiting embodiment: Conversion to M3 glycoform antibodies (FIGS. 3d and 4d); and In a further non-limiting embodiment: Conversion to S(6)2 glycoform antibodies (FIGS. 3e, 6b, 6c, 7b and 7c).

Highly galactosylated antibodies found to have enhanced affinity towards FcγRIIIa receptors and increased effector function for some antibodies. Since galactosylation have beneficial effect in either ADCC or CDC activity, it is ideal to convert all the antibodies to G2-glycoforms. Also, the presence of terminal galactose in N-glycans is required to attach sialic acid to produce sialylated antibodies. Our results demonstrate that all the antibodies, irrespective of type and size, can be modified to single homogeneous G2 glycoforms from heterogeneous population using this technology. In addition, the batch to batch variability of galactosylation of antibodies can also be addressed by modulating the galactosylation to desired level as per regulatory needs.

Figure 6:
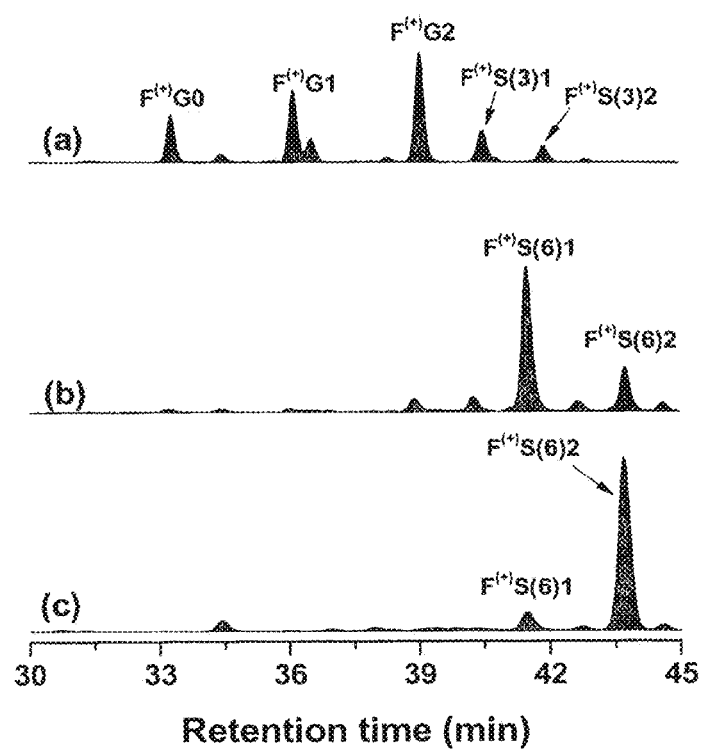
FIG. 6: Conversion of EG2-hFc monoclonal antibody into sialylated forms using recombinant a human α(2,6) sialyltransferase. HILIC-HPLC profiles of N-glycans from (a) unmodified EG2-hFc antibody, modified to sialylated forms using (b) 5 μg of enzyme in two reaction rounds of 48 h each and (c) 10 μg of enzyme with four reaction rounds of 24 h each with recycling and reusing of enzyme from previous round along with 2 μg of fresh enzyme.

The presence of terminal sialic acid in N-glycans is necessary for anti-inflammatory activity of antibodies and the sialic acid has to be linked at (2-6) to galactose. Sialylated IgGs are good therapeutic agents to treat autoimmune and inflamatory diseases. The method of the present invention was used to produce S(6)2-glycoform antibodies with terminal sialic acid at α(2-6) linkage. Antibodies with partial galactosylation were first galactosylated to produce G2-glycoform antibodies. In this, an α(2-3) specific neuramindase was used instead of non-specific neuramindase to avoid any possibility of trace neuraminidase activity while performing sialylation in the second stage. The formation of mono-sialylated antibodies was found to quicker than formation to disialylated forms. This is due to the fact that rate of formation of monosialylated fraction with the addition of sialic acid to galactose on α(1-3) mannose branch is 8 to 11-fold higher than the addition of second sialic acid to α(1-6) arm to form disialylated. By optimizing reaction conditions and using removal of inhibitory byproduct CMP, conversion up to 76% of S(6)2 and 18% of S(6)1 glycoforms was obtained (FIG. 6c). This demonstrates that complete conversion to S(6)2 glycoforms is feasible by optimizing the reaction conditions.

Figure 9:
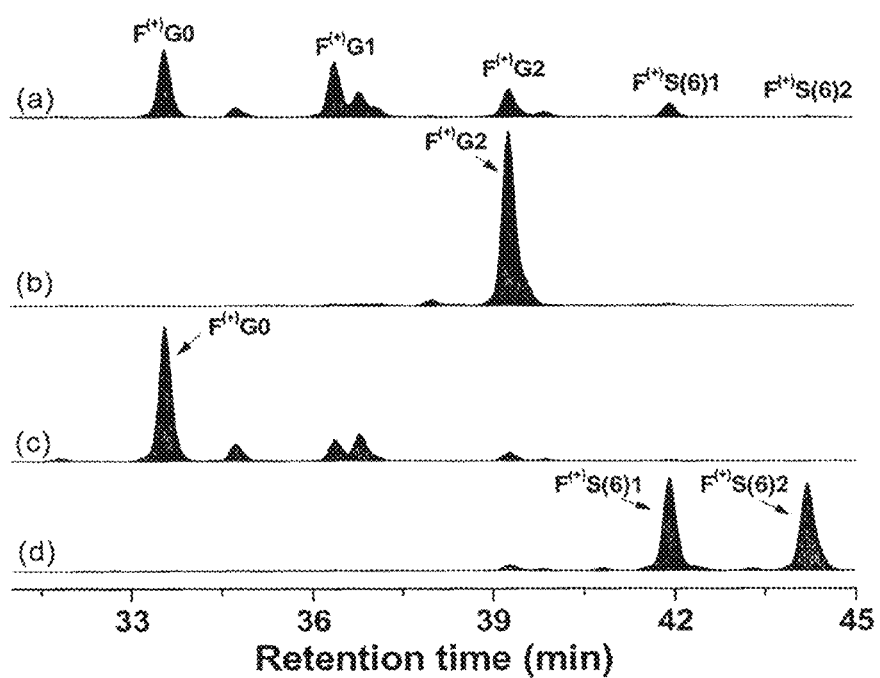
FIG. 9: HILIC-HPLC profiles of N-glycans of (a) unmodified serum IgGs, (b) modified to G2 glycoforms, (c) G0 glycoforms and (d) sialylated glycoforms.

Intravenous Immunoglobulins (IVIGs) are purified antibodies from pooled blood by donors. The major fraction of serum IVIGs are IgGs and among those only about 10% are sialylated forms. They are used for variety of treatments including treating autoimmune disorders and inflammatory diseases. In addition, there has been recent interest to use IVIGs for desensitization therapy for organ transplant. The mechanism behind the effect of IVIGs on various treatments is currently not established. It is believed that the sialylated antibodies are anti-inflamatory and are responsible for therapeutic effect during the treatment of autoimmune disorders and inflammatory diseases. The current method of modifying the IVIGs to homogeneous glycosylated forms provides the opportunity to determine the function of glycosylation of these IVIGs in various applications. Also, the technology can be implemented to modify IVIGs to desired glycosylation pattern during the IVIGs fractionation and purification. This would reduce the amount of IVIGs needed to inject per patient and hence benefit more patients from the same quantity. We have demonstrated that the polyclonal serum IVIGs can be converted to either G0 or G2 or sialylated forms by using this modification method (FIG. 9).

The method of the invention was successfully used to produce G0-glycoforms of three monoclonal antibodies (FIGS. 3c, 4c and 5c) and polyconal serum IgGs from their heterogeneous population. Antibodies with absence of galactose are of no advantage with regard to their effector function, but removal of terminal galactose is necessary to link bisecting GlcNAc. Antibodies containing N-glycans with bisecting GlcNAc was found to have enhanced ADCC activity [Davies, J., Jiang, L. Y., Pan, L. Z., LaBarre, Mi, Anderson, D., Reff. M, 2001. *Expression of Gntiii in a Recombinant Anti-Cd20 Cho Production Cell Line: Expression of Antibodies with Altered Glycoforms Leads to an Increase in Adcc through Higher Affinity for Fc Gamma Riii. Biotechnology and Bioengineering* 74, 288-294; Umana, P., Jean-Mairet, J., Moudry, R., Amstutz, H., Bailey, J. E, 1999. *Engineered Glycoforms of an Antineuroblastoma Igg1 with Optimized Antibody-Dependent Cellular Cytotoxic Activity. Nature Biotechnology* 17, 176-180]. The present method of modification of antibodies can be applied to produce antibodies with bisecting GlcNAc antibodies (A2B-glycforms) by addition of GlcNAc to core mannose of G0 glycoforms with mannosyl-glucosamine transferase III enzyme. The A2B glycoforms can be galactosylated further to obtain A2BG2 glycoform antibodies. This method can also be used to generate glycoforms that are not conventionally obtained by cell culture. For example, M3(F$^+$) form of antibodies are not part of glycosylation pathway since, in general, GlcNAc is attached to mannose on one arm before the other two mannose residues in M5 structure are cleaved to form hybrid structure.

Figure 4:
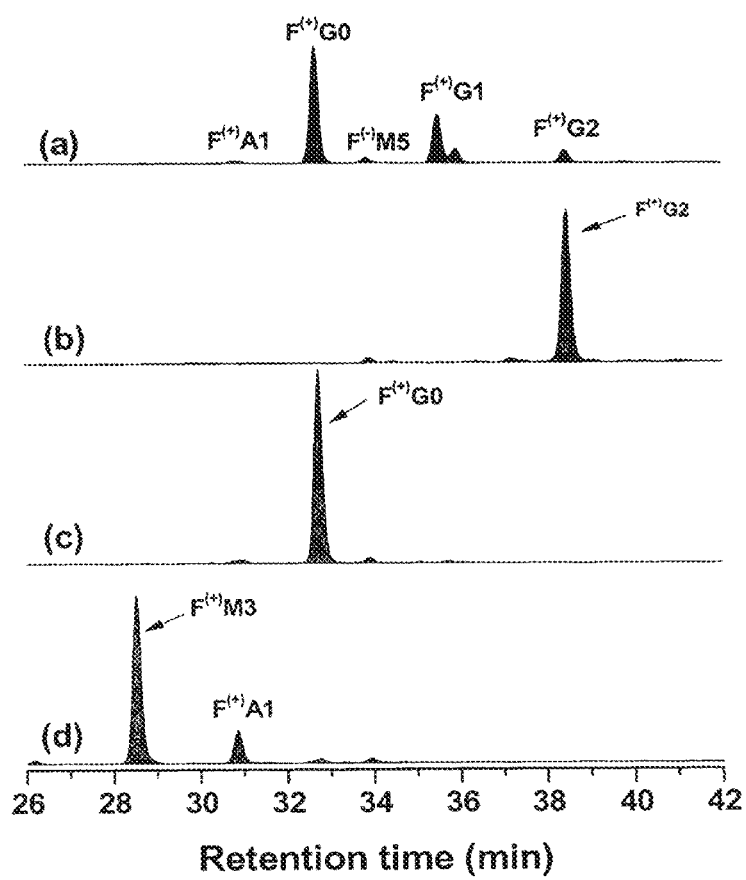
FIG. 4: HILIC-HPLC profiles of N-glycans of Cetuximab® antibodies modified to different homogeneous glycoforms: (a) unmodified control (b) modified to G2 glycoforms (c) modified to G0 glycoforms and (d) modified to M3 glycoforms.
Figure 5:
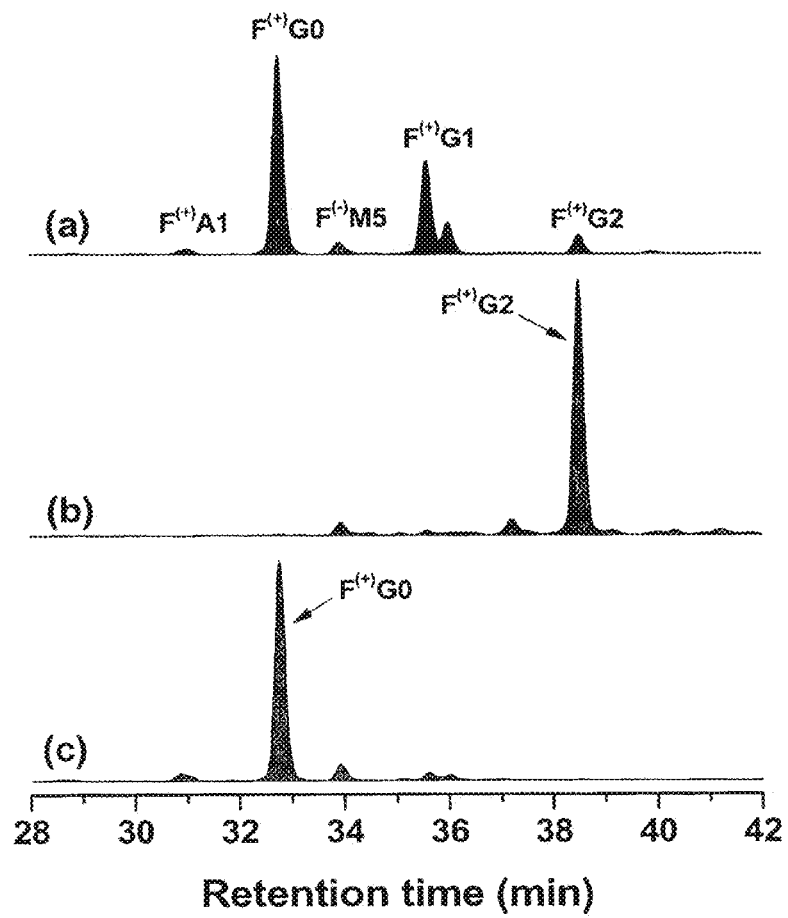
FIG. 5: HILIC-HPLC profiles of N-glycans of aIL8-hFc antibodies modified to different homogeneous glycoforms: (a) unmodified control (b) modified to G2 glycoforms (c) modified to G0 glycoforms.

The method of the invention was used to produce antibodies core (M3) structure (FIGS. 3d and 4d). This allows for investigation of the functional abilities of IgGs containing these N-glycan structures. This method is not limited to produce only glycoforms presented herein but to generate antibodies with other desired glycan structures as required. This method can be used not only to produce antibodies with desired glycoforms in a laboratory scale to study their clinical efficacy but also can be scaled up to production scale for established therapeutic antibodies.

The method of the invention can be provided as a kit that comprises the reaction buffer, wash buffer, elution buffer and neutralization buffer in addition to an affinity ligand solid support. The reaction buffer may contain one or more of the following non-limiting enzymes: Mannosyl-glucosamine transferases (MGAT1, MGAT2 and MGAT3); Galactosyltransferases (β4GalT1, β4GalT2, β4GalT3, β4GalT4, β4GalT5, β4GalT6, β4GalT7), Sialyltransferases (ST6Gal1, ST6Gal2); Mannosidases (α Mannosidase-I, α Mannosidase-II, α(1-2) Mannosidase, α(1-6) Mannosidase, α(1-2,3) Mannosidase, α(1-2,3,6) Mannosidase); Hexosaminidases (β-N-acetylhexosaminidase, β-N-Acetylglucosaminidase, α-N-Acetylglucosaminidase); Galactosidases (β-galactosidase, β(1-4) galactosidase, α(1-3,6) galactosidase); Sialidases (α(2-3,6,8) sialidase, α(2-3) sialidase), fucosidases (α-L-Fucosidase, α(1-6) fucosidase, α(1-2) fucosidase, α(1-3,4) fucosidase, and α(1-2,3,4) fucosidase). The kit may also include instructions for use as well as any equipment.

To summarize, the present enzymatic methods in aspects produce single glycoform mAbs from a heterogeneous glycoform mAb population in a single step in such a manner such that a desired single glycoform profile can be achieved and used for immunotherapy of cancers, autoimmune disorders and inflammatory disorders. In the method, the heterogeneous glycoform mAb is affinity bound and treated in a one-step manner to produce a desired single glycoform without release of the mAb from the affinity ligand as it is being reacted and while exposing the Fc region of the mAb for modification. The method of the invention can be applied to any desired antibody from different sources and repeated to design a specific single glycoform as desired.

In further aspects, the present enzymatic methods produce single glycoform polyclonal Abs from a heterogeneous glycoform polyclonal population in a single step in such a manner such that a desired single glycoform profile can be achieved and used for immunotherapy of cancers, autoimmune disorders and inflammatory disorders. In the method, the heterogeneous glycoform polyclonal antibody (as provided for example from a serum source) is affinity bound and treated in a one-step manner to produce a desired single glycoform without release of the antibody from the affinity ligand as it is being reacted and while exposing the Fc region of the antibody for modification. The method of the invention can be applied to any desired antibody from different polyclonal sources and repeated to design a specific single glycoform as desired.

The method provides a composition of biopharmaceutical that is tailored to a clinical indication whether a cancer, autoimmune disorder or an inflammatory disorder. The affinity bound single glycoform mAbs or polyclonal antibody so produced can be provided as a composition for therapeutic use. As a biopharmaceutical composition, it may further comprise pharmaceutically acceptable carriers, and optionally, at least one additional therapeutic agent. In further aspects of the invention, the biopharmaceutical composition comprises at least one immunoconjugate, wherein the immunoconjugate comprises a single glycoform antibody as provided herein that binds to a desired receptor and a cytotoxic agent; a pharmaceutically acceptable carrier; and optionally, at least one additional therapeutic agent.

The invention further provides a liquid aqueous biopharmaceutical composition comprising a therapeutically effective amount of a single glycoform antibody as provided herein in a buffered solution forming a composition having a desirable pH (in aspects between about 4 and about 8, in aspects about 5-7, still in more aspects about 6-6.5, however, the pH depends on the antibody contained and is not limited to these values) which is easily administrable to a subject.

Biopharmaceutical compositions of the present invention are normally administered via parenteral routes such as injection (e.g. subcutaneous, intravenous, intramuscular or intraperitoneal injection) or percutaneous, mucosal, nasal or pulmonary administration, but may also be orally administered. The biopharmaceutical compositions of the invention can be normally supplied in sealed and sterilized plastic or glass containers having a defined volume such as vials, ampules or syringes or a large volume such as bottles. In terms of convenience, prefilled syringes are preferred.

In one embodiment of the invention, the liquid aqueous biopharmaceutical composition is suitable for injection. In a further embodiment, the formulation is suitable for single use sc injection. In another embodiment, the concentration of the single glycoform antibody in the liquid aqueous pharmaceutical composition is about 1-150 mg/ml. In yet another embodiment, the concentration of the single glycoform antibody in the composition is about 50 mg/ml. The amount of single glycoform antibodies contained in compositions of the present invention is typically about 0.1-200 mg/ml, in aspects about 1-120 mg/ml, in more aspects about 2-22.5 mg/mL, depending on the type of the disease to be treated, the severity of the disease, the age of the patient and other factors.

Biopharmaceutical compositions of the present invention may further comprise isotonizing agents, e.g., polyethylene glycol; and sugars such as dextran, mannitol, sorbitol, inositol, glucose, fructose, lactose, xylose, mannose, maltose, sucrose, trehalose and raffinose.

Single glycoform antibody-containing solution biopharmaceutical compositions of the present invention may further comprise diluents, solubilizing agents, excipients, pH-modifiers, soothing agents, buffers, sulfur-containing reducing agents, antioxidants or the like, if desired. For example, sulfur-containing reducing agents include N-acetylcysteine, N-acetylhomocysteine, thioctic acid, thiodiglycol, thioethanolamine, thioglycerol, thiosorbitol, thioglycolic acid and salts thereof, sodium thiosulfate, glutathione, and sulfhydryl-containing compounds such as thioalkanoic acid having 1 to 7 carbon atoms. Antioxidants include erythorbic acid, dibutylhydroxytoluene, butylhydroxyanisole, .alpha.-tocopherol, tocopherol acetate, L-ascorbic acid and salts thereof, L-ascorbyl palmitate, L-ascorbyl stearate, sodium bisulfite, sodium sulfite, triamyl gallate, propyl gallate or chelating agents such as disodium ethylenediamine tetraacetate (EDTA), sodium pyrophosphate and sodium metaphosphate. Other common additives may also be contained, e.g., inorganic salts such as sodium chloride, potassium chloride, calcium chloride, sodium phosphate, potassium phosphate and sodium bicarbonate; and organic salts such as sodium citrate, potassium citrate and sodium acetate.

Biopharmaceutical compositions of the invention can also be used in conjunction with organ transplantation, as a composition to bathe/perfuse tissues and/or organs for transplantation.

With the provision of methods to manufacture desirable therapeutic single glycoform antibodies, novel methods of treatment of cancers, autoimmune disorder and inflammatory disorders are encompassed herein with the use of the novel method to produce a substantially homogeneous single glycoform mAb for such treatment.

The disclosures of each and every patent, patent application, and publication cited herein are hereby incorporated herein by reference in their entirety.

While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

The examples are illustrative and employ, unless otherwise indicated, conventional techniques of molecular biology, microbiology, recombinant DNA, and immunology, which are within the skill of the art. Such techniques are explained fully in the literature. See, for example, Molecular Cloning A Laboratory Manual, 2nd Ed., ed. by Sambrook, Fritsch and Maniatis (Cold Spring Harbor Laboratory Press, 1989); DNA Cloning, Volumes I and II (D. N. Glover ed., 1985); Culture Of Animal Cells (R. I. Freshney, Alan R. Liss, Inc., 1987); Immobilized Cells And Enzymes (IRL Press, 1986); B. Perbal, A Practical Guide To Molecular Cloning (1984); the treatise, Methods In Enzymology (Academic Press, Inc., N.Y.); Gene Transfer Vectors For Mammalian Cells (J. H. Miller and M. P. Calos eds., 1987, Cold Spring Harbor Laboratory); Methods In Enzymology, Vols.

154 and 155 (Wu et al. eds), Immunochemical Methods In Cell And Molecular Biology (Mayer and Walker, eds., Academic Press, London, 1987); Antibodies: A Laboratory Manual, by Harlow and Lane s (Cold Spring Harbor Laboratory Press, 1988); and Handbook Of Experimental Immunology, Volumes I-IV (D. M. Weir and C. C. Blackwell, eds., 1986).

EXAMPLES

Materials and Methods

Antibodies: Three monoclonal antibodies were used in these studies. A chimeric monoclonal antibody (EG2-hFc), in which EG2 portion from a camelid antibody is fused with Fc fragment of a human IgG1, comprises only heavy chains and ~80 KDa in size. This antibody was produced from a Chinese hamster ovary cell line (CHO-EG2) provided by Biotechnology research institute, Montreal. Cetuximab, an IgG1-type full size chimeric antibody of ~150 KDa in size, was provided by Biotechnology Research Institute. Both these antibodies target epidermal growth factor receptor (EGFR) on tumor cells. A humanized monoclonal antibody (aIL8-hFc) was produced from a Chinese hamster ovary cell line (CHO-DP12, ATCC #CRL-12445). This is an IgG1-type humanized antibody (150 KDa in size) that targets interleukin-8 (IL8). This antibody is as anti-inflammatory agent, which inhibits IL8-mediated neutrophil chemotaxis.

Generalized workflow for in-vitro modification of N-glycans of antibodies: The in-vitro modification of N-glycans of antibodies was performed by binding antibodies to an affinity ligand. The general steps involved for the modification is presented in FIG. 1. For the current studies, HP spin-trap Protein-A columns of 1 mg human IgG binding capacity (GE Life Sciences, Cat #28903132) were used. The columns were washed twice with 700 μL of phosphate buffer saline (PBS) and then solution containing antibodies of desired quantity were loaded on to the column. The columns were incubated at room temperature for 10 min (shaking by hand at an interval of 3 min) to capture the antibodies. The flow-through was discarded and the columns were washed four times with 700 μL of PBS and once with the reaction buffer (designed for particular modification as described in below sections). Then the reaction mixture, containing specific enzymes, co-factors (if needed) and nucleotide sugars (if needed) in modification buffer, was added to the columns. The columns were incubated at 37° C. for specific time period (as specified in below sections). To keep the resin suspended in solution, the incubation was done by keeping the columns rolling in a tray on an orbital shaker at 120 RPM. After that, the reaction mixture was removed and, if needed, multiple rounds of reaction were performed with the same reaction mixture. The reaction round may involve reusing of enzyme from previous round by recycling it from inhibitory byproducts. After final round, the column was washed with 700 μL of PBS for 5 times. If a second stage modification from one glycoform to another is involved, the columns were washed once with the 700 μL of corresponding reaction buffer and the modification was performed with reaction mixture specific for the conversion. After all the stages of modifications, the antibodies were eluted with 0.1 M Glycine-HCl buffer (pH 2.7) and neutralized to pH ~7.2 with 1 M TRIS-HCl solution (pH 9.0).

Galactosylation of antibodies: aIL8-hFc antibodies were used to demonstrate the galactosylation of antibodies bound to protein-A. About 60 jig of antibody was loaded on to protein-A columns. This is one stage modification with single reaction round and the buffer is 25 mM TRIS, 50 mM NaCl, adjusted to pH 7.5@25° C. with HCl (called here as B2 buffer). The reaction mixture consists of either 30 or 70 milli-units of (1,4) galactosyltransferase (SIGMA-ALDRICH™, Cat #48279), 1 mM UDP-galactose (SIGMA-ALDRICH™, Cat #U4500), 10 mM MnCh in 150 μL of G2 buffer. The incubation time for modification is either 24 h or 48 h.

Production of G2-glycoform antibodies: The conversion of heterogeneous mixture of glycoforms to homogeneous G2-glycoform antibodies was demonstrated using three types of antibodies (EG2-hFc or aIL8-hFc or Cetuximab). About 50 μg of each antibody was loaded on to protein-A column for each case. This modification was performed in single stage and one reaction round. The reaction mixture consisting of 100 milli-units of (1,4) galactosyltransferase, 1.5 mM UDP-galactose, 10 mM MnCh and 200 units of neuraminidase (NEWENGLAND BIOLABS™, Cat #P0720) in 150 μL B2 buffer. The columns were incubated at 37° C. and shaking for 48 hours.

Production of S2-glycoform antibodies: The conversion to homogeneous S2-glycoform antibodies was demonstrated using EG2-hFc or aIL8-hFc antibody. For initial experiments, Rat α(2-6) sialyltransferase (rST6Gall) tagged with GFP was used. GFP-tagged rat ST6Gall (rST6Gall-GFP) was a gift from Dr. Kelly Moremen at Complex Carbohydrate Research Center, Georgia, United States. About 50 μg of EG2-hFc antibody was loaded on to protein-A columns and the conversion is performed in two stages. The first stage is converting to G2-glycoform as described above but α(2-3) neuraminidase (NEWENGLAND BIOLABS™, Cat #P0728) was used instead of neuraminidase. In the second stage, the reaction was performed in two reaction rounds of 48 h each with reaction mixture of 4.5 μg of rST6Gal1-GFP and 1 mM CMP-Neu5Ac in B2 buffer. For the further S2 modifications, recombinant human α(2-6) sialyltransferase (hST6Gal) (ROCHE CUSTOM BIOTECH™, Cat #07012250103) was used. About 50 μg of EG2-hFc or 75 μg of aIL8-hFc was used for modifying to S(6)2 form. After the first stage of converting to G2 glycoforms, S(6)2 modification was performed with 5 μg of hST6Gal and 1 mM CMP-Neu5Ac in two reaction rounds of 48 h each. In another conversion, modification to S(6)2 was done with 10 μg of hST6Gal and 1 mM CMP-Neu5Ac in four reaction rounds of 24 h each with recycling the enzyme from previous round and transferring to reaction mixture containing 2 μg of hST6Gal and 1 mM CMP-Neu5Ac to use it in next round.

Production of GO-glycoform antibodies: The conversion to homogeneous G0-glycoform antibodies was demonstrated using three types of antibodies (EG2-hFc or aIL8-hFc or Cetuximab). About 50 μg of antibody was loaded on to protein-A columns. The conversion is performed in one stage consisting of single reaction round but with the following changes. The reaction buffer for this conversion is 25 mM TRIS, 50 mM NaCl and pH 6.6@25° C. (called here as B1 buffer). The reaction mixture consisted of 100 units of β(1,4) galactosidase (NEWENGLAND BIOLABS™, Cat #P0730) and 200 units of Neuraminidase in 150 μl. BI buffer. The columns were incubated at 37° C. and shaking for 48 hours.

Production of M3-glycoform antibodies: The conversion to homogeneous M3-glycoform antibodies was demonstrated using EG2-hFc and Cetuximab. About 50 μg of antibody was loaded on to protein-A column and the conversion is performed in two stages. The first stage is converting to G0-glycoform as described above. The G0-glycoforms were further converted to M3-glycoforms in the second stage using reaction mixture of 20 units of β-N-acetylgiucosaminidase (NEWENGLAND BIOLABS™, Cat #P0732) in 150 μL B1 buffer. For Egg- hFc, the conversion is performed with single reaction round of 72 h incubation. For Cetuximab, the second stage consisted of two reaction rounds with 48 h incubation in each.

Modification of serum IgGs: Polyclonal IgGs used for modification were from AB blood type human serum (SIGMA-ALDRICH™, Cat #H4522). Serum was diluted in PBS and ~250 ug of IgGs were loaded on to protein A columns. The modifications to different glycoforms were performed using the following conditions:

| Modification | Stages | Buffer | Reagents | Incubation time |
|---|---|---|---|---|
| G0 | Stage 1 | 25 mM BIS-TRIS, 50 mM NaCl, pH 6.6 @ 25° C. | 3 units/μL (1,4) galactosidase, 3 units/μL neuraminidase | 48 h |
| G2 | Stage 1 | 25 mM TRIS, 50 mM NaCl, pH 7.5 @ 25° C. | 2 milli-units/μL β (1,4) galactosyltransferase, 3 mM UDP-galactose, 10 mM MnCl$_2$, 3 units/μL neuraminidase | 48 h |
| SA | Stage 1 | 25 mM TRIS, 50 mM NaCl, pH 7.5 @ 25° C. | 2 milli-units/μL β (1,4) galactosyltransferase, 3 mM UDP-galactose, 10 mM MnCl$_2$ | 48 h |
| | Stage 2 | 25 mM TRIS, 50 mM NaCl, pH 7.5 @ 25° C. | 100 μg/mL (2,6) sialyltransferase, 3 mM CMP-Neu5Ac | 48 h (round 1) 72 h (round 2) |

Glycoprofile analysis: The glycans from the antibodies were released with PNGaseF digestion. A solution containing 50 μg of antibody (either control or modified) was loaded on to protein A column and incubated at room temperature for 10 min (with shaking by hand at 3-min interval). The flow-through from the column was discarded and the column was washed 3 times with 700 uL of PBS. Then reaction mixture containing 10 units of PNGaseF (PROMEGA™, Cat #V4831) in 200 uL of 20 mM phosphate buffer [80% 20 mM Na$_2$HPO$_4$ and 20% 20 mM NaH$_2$PO$_4$ (v/v)] was added to the column and incubated at 37° C. for 24 hours. The columns were incubated by keeping them rolling in a tray on an orbital shaker at 120 RPM to keep the resin in suspension. The flow-through containing released glycans into the reaction buffer was collected and filtered through a pre-washed 10 KDa cut-off filter to remove PNGaseF. The filtered glycans were dried under vacuum at room temperature. Glycans were labelled with 5 μL of 2-aminobenzamide (2-AB) labelling solution (0.4 M 2-AB and 1 M NaBH$_3$CN in 30% acetic acid/70% DMSO) by incubating at 65° C. for 2 h. Excess 2-AB was removed using a HypersepDiol SPE cartridge (THERMOSCIENTIFIC, Cat #60108-571) by normal phase extraction. Each, cartridge was washed with 1 mL milli-Q H$_2$O, conditioned with 4 mL Acetonitrile. The solution containing labelled glycans diluted with 45 μL of acetonitrile was added to the cartridge and incubated for 15 min. Then the cartridge was washed with 1 mL Acetonitrile and 5 mL 96% Acetonitrile. The glycans were eluted with 1.2 mL milli-Q H$_2$O. The labelled glycans were analyzed by hydrophobic interaction chromatography mode with a Waters HPLC using Xbridge BEH Amide column (WATERS CORPORATION™, Cat #186004870). Each peak was assigned a glucose unit value calculated using a dextran ladder standard. Structures corresponding to each peak were assigned by reference to the Glycobase 3.2 database (glycobase.nibrt.ie, NIBRT™, Dublin, Ireland).

N-Glycan profiles of antibodies: The profiles of N-glycans in Fc region of EG2-hFc, Cetuximab and aIL8-hFc are presented in FIGS. 3a, 4a and 5a, respectively. The structures identified in all the three antibodies were fucosylated bi-antennary glycans. All the antibodies consist of a heterogeneous population with respect to their glycan structures, especially in terms of the extent of galactosylation and sialylation. The glycans of EG2-hFc antibodies were highly galactosylated and moderately sialylated compared to Cetuximab and aIL8-hFc. The extent of glycosylation with a particular sugar unit (galactose or sialic acid) on the N-glycan is represented by a galactosylation or sialylation index, which is defined as $$\frac{X_2 + 0.5 * X_1}{X_0 + X_1 + X_2}$$

where the fraction of each glycan with an X sugar unit on both antennae ($X_2$), on one antenna ($X_1$) and neither antenna ($X_0$) is represented in the equation. The galactosylation index and sialylation index correspond to the cases when X represents galactose and sialic acid, respectively. The major fraction of the EG2-hFc antibody consists of glycans with terminal galactose on both arms (G2-glycoforms) accounting for ~35%, of the total glycans analyzed while the fraction consisting of glycans with galactose on either one of the arms (G1-glycoform) accounts for 30%. The fraction of the EG2-hFc antibody with no galactose (G0-glycoforms) is 13.5%. Sialylation was significant in this antibody with 11.5% of the antibody with glycans bearing sialic acid on one arm (S(3)1-glycoforms) and 5.5% antibodies with completely sialylated glycans (S(3)2-glycoforms). The corresponding galactosylation and sialylation indices are 0.64 and 0.12, respectively. On the other hand, galactosylation is low and sialylation is negligible in Cetuximab and aIL8-hFc. The predominant fractions in both Cetuximab and aIL8-hFc are G0-glycoforms accounting for ~55% and the fraction of G1-glycoforms was ~34%. The galactosylation index for both Cetuximab and aIL8-hFc is ~0.22.

Figure 2:
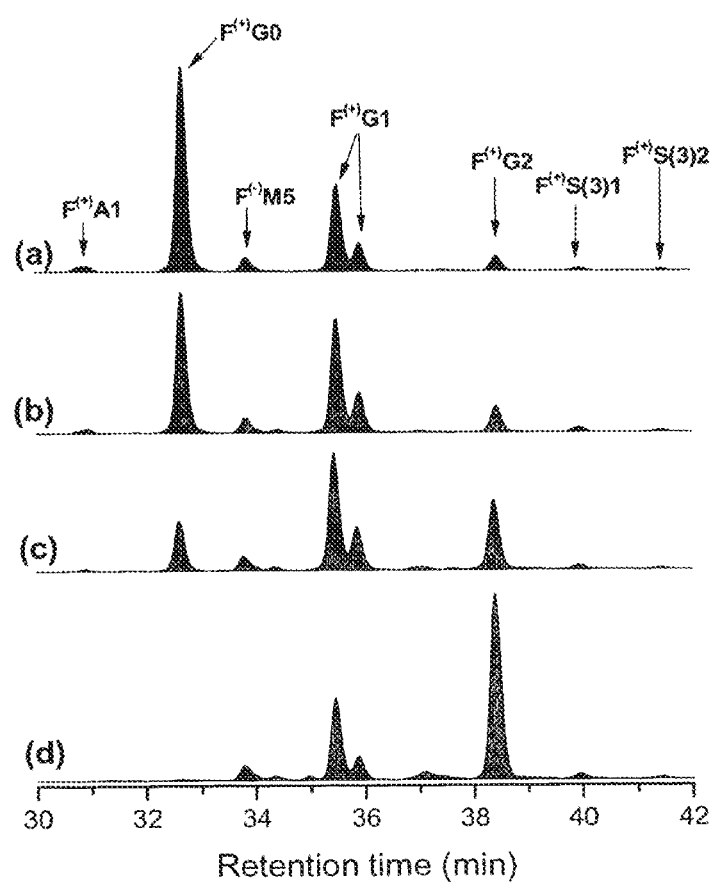
FIG. 2: HILIC-HPLC profiles of aIL8-hFc N-glycans subjected to galactosylation modification with different β(1, 4) galactosyltransferase enzyme and reaction time as follows (a) ummodified control (b) 30 milli-U of enzyme and 24 h (c) 70 milli-U of enzyme and 24 h (d) 70 milli-U of enzyme and 48 h.
Figure 3:
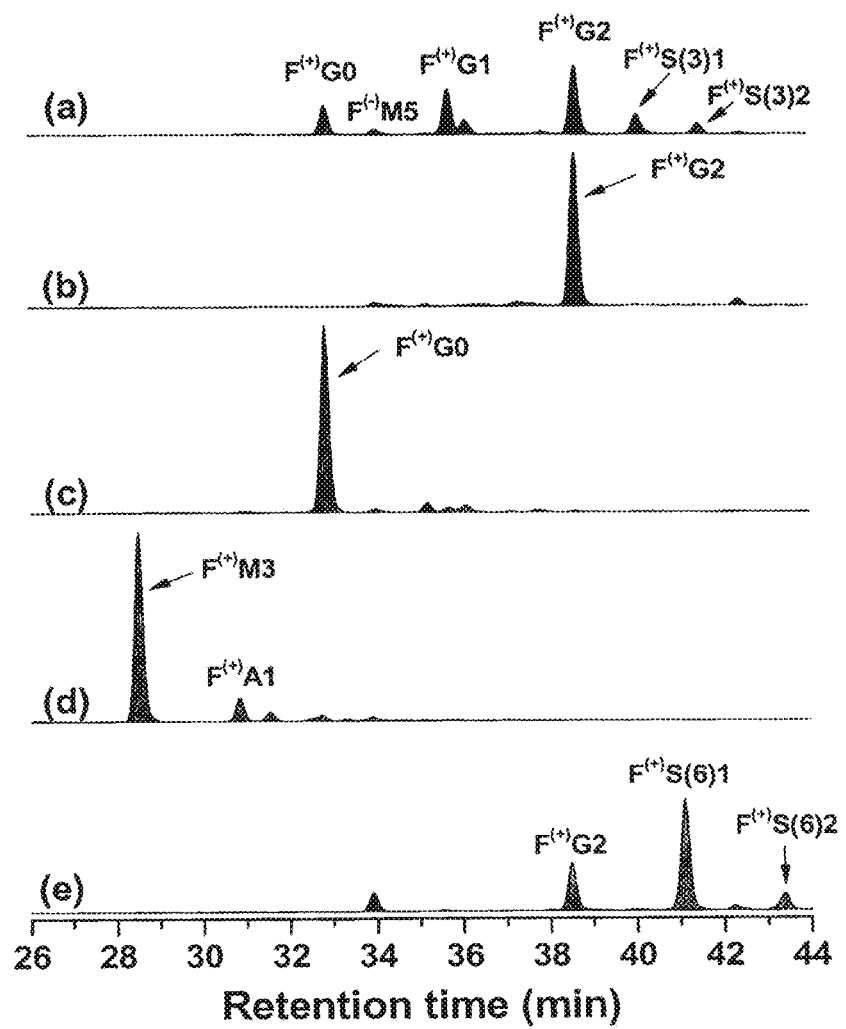
FIG. 3: HILIC-HPLC profiles of N-glycans of EG2-hFc antibodies modified to different homogeneous glycoforms: (a) unmodified control (b) modified to G2 glycoforms (c) modified to G0 glycoforms (d) modified to M3 glycoforms and (e) modification aimed to S(6)2 glycoforms using Rat ST6Gal1-GFP enzyme.

Galactosylation of antibodies: The N-glycans of each antibody bound to the affinity ligand, (protein-A immobilized to sepharose) was modified by strategic enzymic reactions. Initial experiments were performed to find optimal enzyme concentration and times of incubation using aIL8-hFc. This serves as a model for a typical full size humanized IgG1-type therapeutic antibody. Galactosylation by linkage of a galactose by β(1-4) to N-acetlyglucosamine was performed using the β(1-4) galactosyltransferase from bovine milk, which is 44 KDa enzyme. The rate of addition of galactose depends on enzyme concentration, type and pH of buffer, and time of incubation. The operational pH for strong interaction of protein-A and antibodies is 6.0 to 8.0, with optimum range of 6.5-7.5. The optimum pH for β(1-4) galactosyltransferase is around 7.0-7.5. Hence the pH of the reaction buffer is set to 7.5 @ 25° C. (pH of 7.22 @ 37° C.). Galactosyltransferases require $Mn^{2+}$ ions as cofactor, typically provided at a concentration of 10 mM. The results on changes in the galactosylation index of aIL8-hFc antibody with different enzyme concentrations and times of incubation are presented in FIG. 2. The galactosylation index of unmodified aI18-hFc antibody was 0.22 (FIG. 2a). The galactosylation index was increased to 0.32 when modification was performed with 30 milli-U of galactosyltransferase per 60 μg of antibody for 24 h (FIG. 2b) and the index was increased further to 0.56 when the enzyme concentration was increased to 70 milli-U (FIG. 2c). When the time of incubation was increased to 48 h with 70 milli-U of enzyme, the galactosylation index was increased to 0.75 (FIG. 2d). This demonstrated the ability to perform remodeling of glycans of antibodies when bound to an affinity ligand like protein-A. These results also demonstrate that galactosylation of antibodies can be modulated by varying the enzyme concentration and reaction time.

Modification of glycans to G2 glycoforms: A method to convert heterogeneous population of antibodies to homogeneous glycoforms with fully galactosylated N-glycans was developed. A process to produce completely galactosylated antibodies involved only one stage in which sialic acid was removed from sialylated fractions and the galactose was added to non-galactosylated fractions. Antibodies (like EG2-hFc) have a small fraction of glycans with terminal sialic acid acid which was removed by the neuraminidase, which is 43 KDa enzyme. Neuraminidase catalyzes the removal of N-acetyl neuraminic acid (NeuAc) linked to galactose at efficiency under acidic pH conditions, though it has wide operating pH range from 6.0 to 8.0. The result of this conversion of EG2-hFc to G2-glycoform antibodies by this procedure is presented in FIG. 3b. As noted from the figure, the fractions of antibodies that are non-galactosylated or partially galactosylated were completely galactosylated. The galactosylation index of EG2-hFc was increased to ~0.96. In addition, the 17% of sialylated EG2-hFc antibodies became non-sialylated, yielding single predominant G2-glycoform antibodies. The similar procedure was tested on Cetuximab and aIL8-hFc antibodies and the results are presented in FIGS. 4(b) and 5(b), respectively. For both cases, the G2-glycoform antibodies are single predominant fractions. The galactosylation indices for Cetuximab and aIL8-hFc were increased to ~0.95.

Modification of glycans to G0 glycoforms: A procedure to produce G0-glycoform antibodies, by removal of terminal galactose and sialic acid on N-glycans, was developed and tested on the three antibodies. β(1-4) galactosidase of 94 KDa which catalyzes the removal of galactose linked to N-Acetlyglucosamine by β(1-4) linkage was used in combination with neurmindase. This enzyme operates in the acidic pH range of 5.0-6.0. In order to preserve the activity of galactosidase and neurminidase enzymes while maintaining the strong affinity of antibodies to protein-A, a B1 buffer was designed to operate at ~pH 6.35 @ 37° C. The results of modifying EG2-hFc, Cetuximab and aIL8-hFc to G0-glycoforms are presented in FIGS. 3c, 4c and 5c, respectively. As seen from the figures, all the three antibodies are completely de-galactosylated, and desialylated in the case of EG2-hFc, yielding single predominant glycoforms of non-galactosylated antibodies. The percent yield of conversion of Eg2-hFc, Cetuximab and aIL8-hFc to G0-glycoforms are 85, 94 and 83%, repectively.

Modification of glycans to M3 glycoforms: The M3 glycoforms were obtained by removing the terminal GlcNAc from G0 glycoform antibodies. This produces the core structure of N-glycans by exposing the three mannose units of bi-antennary N-glycans. This modification was performed in two stages. In the first stage, the antibodies were converted to G0 glycoforms and then in the second stage, the terminal GlcNAc was removed. β-N-acetylglucosaminidase, a 71 KDa enzyme which catalyzes the removal of terminal non-reducing GlcNAc linked to glycans, was used for this modification. The enzyme was dissolved in B1 buffer as this enzyme works efficiently in an acidic pH environment. With a single reaction round of 72 h incubation, 80% of EG2-hFc was converted to M3-glycoforms and 11% of antibodies to A1-glycoforms with GlcNAc removed from only one antenna (FIG. 3d). Under similar conditions, only 44% of Cetuximab antibodies were converted to M3 glycoforms and 32% to A1 glycoforms (chromatogram not shown). This shows that conversion was faster with smaller size antibody (Eg2-hFc) compared to Cetuximab, indicating the possibility of encountering higher steric hindrance by the enzyme when accessing the glycans in larger size Cetuximab. However, by using two reaction rounds of 48 h incubation each, 78% M3 glycoforms and 15% A1 glycoforms of Cetuximab were produced (FIG. 4d). This demonstrated the necessary of multiple reaction rounds when the conversion is difficult to obtain in single round, especially when the enzymes are labile.

Figure 7:
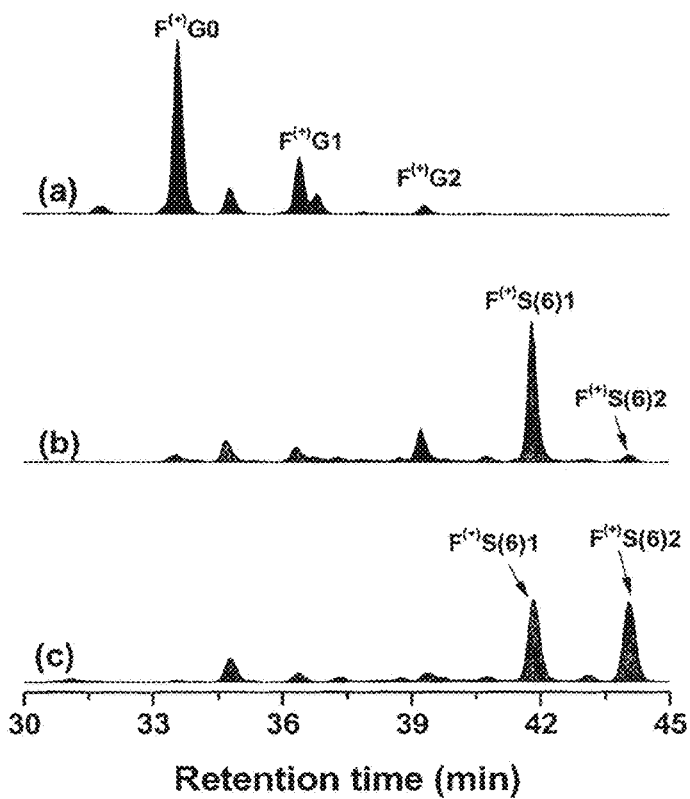
FIG. 7: Conversion of aIL8-hFc monoclonal antibody into sialylated forms using recombinant a human α(2,6) sialyltransferase. HILIC-HPLC profiles of N-glycans from (a) unmodified aIL8-hFc antibody, modified to sialylated forms using (b) 5 μg of enzyme in two reaction rounds of 48 h each and (c) 10 μg of enzyme with four reaction rounds of 24 h each with recycling and reusing of enzyme from previous round along with 2 μg of fresh enzyme.

Modification of glycans to S2 glycoforms: A method was developed to produce sialylated antibodies. Sialic acid can be linked to galactose either by α(2-3) or α(2-6) or α(2-8) linkage. Antibodies produced from CHO cells are sialylated at α(2-3) linkage as in the case of EG2-hFc (FIG. 3a). However human IgGs have sialic acid linked to galactose at either α(2-3) or α(2-6) positions. The anti-inflammatory activity of antibodies was found to be associated with those having α(2-6) linked sialic acid. A two stage process was designed to produce sialylated antibodies with α(2-6) sialic acid. In this two stage process, G2 glycoform antibodies were produced with galactosyltransferase in combination with α(2-3)-specific sialidase (instead of non-specific neuraminidase) to remove α(2-3) sialic acid. The resulting G2-glycoforms were processed further in second stage to convert them to sialylated antibodies by linking sialic acid to galactose at (2-6) linkage using α(2-6) sialyltransferase. The total size of α(2-6) sialyltransferase enzyme (rST6Gal1-GFP) used in our initial studies is of 70 KDa consisting of a ~28 KDa GFP fragment in it. After two rounds of reaction with 48 h incubation in each, 54% of mono sialylated (S(6)1) and 8% of disialylated (S(6)2) EG2-hFc antibodies were produced (FIG. 3e). The presence of GFP fragment in the sialyltransferase used in these studies made the enzyme larger in size which might have provided higher steric hindrance and lowered the catalytic activity of α(2-6) sialyltransferase. For further S(6)2 modifications, recombinant human α(2,6) sialyltransferase (hST6Gal) of 40.6 KDa was used. By 5 μg of hST6Gal in two reaction rounds of 48 h each, all G2 glycoforms of EG2-hFc were converted to sialylated forms with 58% S(6)1 and 17% S(6)2 form (FIG. 6b). While with similar conditions, aIL8-hFc was converted primarily o S(6) 1 glycoform (FIG. 7b). By increasing the enzyme concentration to 10 μg with four reaction rounds of 24 h each and recycling the enzyme from inhibitory CMP byproduct, EG2-hFc was converted to 76% of S(6)2 and 16% of S(6)1 glycoforms (FIG. 6c). However, with the same conditions of modification, aIL8-hFc was converted to 37% S(6)2 and 38% S(6)1 glycoforms (FIG. 7c). The rate of formation of monosialylated fraction with the addition of sialic acid to galactose on α(1-3) mannose branch is 8 to 11-fold higher than the addition of second sialic acid to α(1-6) arm to form disialylated. Because of the larger size of aIL8-hFc, higher enzyme concentration might be needed to enhance the rate of formation of aIL8-hFc to S(6)2 glycoform. Either increasing enzyme concentration and/or more reaction rounds should produce complete S(6)2 glycoforms of aIL8-hFc. Nonetheless, it was demonstrated the N-glycans of antibodies can be converted to S(6)2 glycoforms using this modification process.

Use of Protein G Column as a Comparison with Protein A and Protein G:

TABLE 1

Modification of EG2-hFc antibody to homogeneous glycoforms using two affinity ligand columns (Protein A and Protein G).

| Glycoform | Control | Conversion to G2 form | | Conversion to G0 form | |
|---|---|---|---|---|---|
| | | Protein A | Protein G | Protein A | Protein G |
| $F^{(+)}G0$ | 11.6 | — | — | 88.6 | 86.4 |
| $F^{(+)}G1$ | 28.1 | — | 2.3 | — | — |
| $F^{(+)}G2$ | 36.9 | 93.2 | 90.4 | — | — |
| $F^{(+)}S(3)1$ | 11.7 | — | — | — | — |
| $F^{(+)}S(3)2$ | 6.2 | — | — | — | — |

The modification of antibodies was performed using protein G columns and compared with the modification on protein A columns. The percentages of glycoforms before and after modification were presented in Table 1. The antibody, reagents concentrations and conditions are same as those used in FIG. 3 except the B1 buffer is replaced with buffer containing 25 mM BIS-TRIS and 50 mM NaCl (pH 6.6 @ 25° C.) (B0 buffer) for G0 modifications. As seen from the table, modification of antibodies can be performed using protein G with slightly lesser efficiency.

Figure 8:
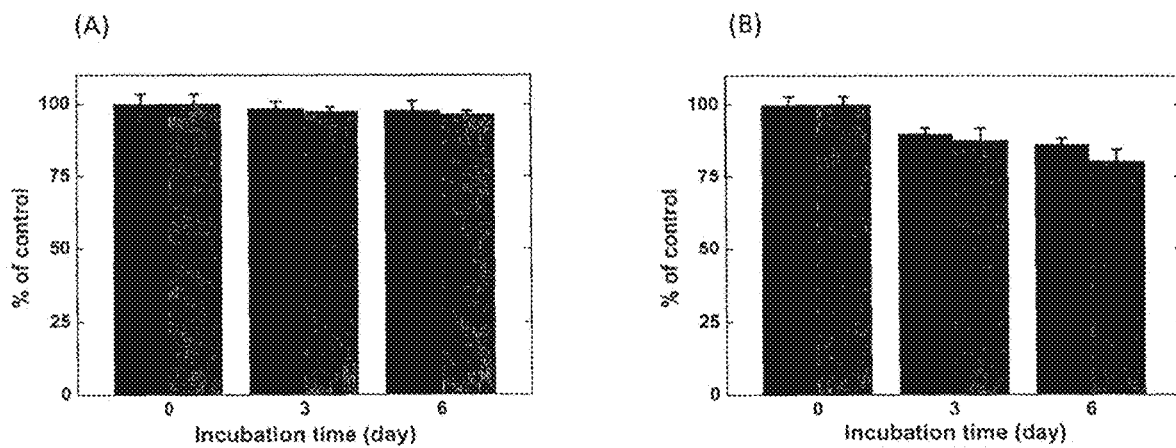
FIG. 8: Stability of antibody binding to affinity ligands during the incubation with reaction buffers. aIL8-hFc antibody was bound to (A) Protein A or (B) Protein G and incubated for different time points in B2 buffer (black bars) or B0 buffer (gray bars). The antibody eluted after incubation time and the measured concentrations were normalized to the percentage of unincubated control (day 0).

The strength of the bond between antibody and affinity ligands was tested during the incubation with buffers used for modification. This provides information about the loss of antibody, if any, during the modification process. Equal amounts of aIL8-hFc antibody were bound to either protein A or protein G and incubated in either B2 or B0 buffer for different time points before eluting the antibody. The antibody concentrations were measured and normalized to the amount initially bound on day 0 (control). The results are presented in FIG. 8. The antibody remained stably bound to protein A throughout the incubation time in both buffers (FIG. 8A). However, loss of antibody with incubation time that was bound to protein G was observed, especially in B0 buffer. From these studies, it can be concluded that protein A is efficient for both the modification and reducing the loss of antibodies during the process. Protein G may still be utilized.

Modification of Serum IgGs to Different Glycoforms:

The modification of human serum polyclonal IgGs was demonstrated by capturing them on to protein A and converting them to various glycoforms (FIG. 9). The modification to G0 glycoforms resulted in 62% conversion of IgGs whereas converstion to G2 glycoforms resulted in 96% conversion. Modification to S(6)2 glycoforms resulted in formation of 43% S(6)1 and 46% S(6)2 glycoforms. Further optimization of the S(6)2 modification procedure including recycling of enzyme to remove inhibitory byproduct CMP has to be implemented to increase the efficiency of conversion. Nonetheless, the method would be able to convert serum IgGs to various glycoforms, including but not limited to, G0, G2 and S(6)2 glycoforms.

REFERENCES

Anthony, R. M., Kobayashi, T., Wermeling, F., Ravetch, J. V., 2011. Intravenous Gammaglobulin Suppresses Inflammation through a Novel T(H)2 Pathway. Nature 475, 110-U133.

Anthony, R. M., Nimmerjahn, F., Ashline, D. J., Reinhold, V. N., Paulson, J. C., Ravetch, J. V., 2008. Recapitulation of Ivig Anti-Inflammatory Activity with a Recombinant Igg Fc. Science 320, 373-376.

Barb, A. W., Brady, E. K., Prestegard, J. H., 2009. Branch-Specific Sialylation of Igg-Fc Glycans by St6gal-I. Biochemistry 48, 9705-9707.

Barb, A. W., Meng, L., Gao, Z., Johnson, R. W., Moremen, K. W., Prestegard, J. H., 2012. Nmr Characterization of Immunoglobulin G Fc Glycan Motion on Enzymatic Sialylation. Biochemistry 51, 4618-4626.

Barb, A. W., Prestegard, J. H., 2011. Nmr Analysis Demonstrates Immunoglobulin G N-Glycans Are Accessible and Dynamic. Nat Chem Biol 7, 147-153.

Boyd, P. N., Lines, A. C., Patel, A. K., 1995. The Effect of the Removal of Sialic Acid, Galactose and Total Carbohydrate on the Functional Activity of Campath-1h. Molecular Immunology 32, 1311-1318.

Davies, J., Jiang, L. Y., Pan, L. Z., LaBarre, M. J., Anderson, D., Reff, M., 2001. Expression of Gntiii in a Recombinant Anti-Cd20 Cho Production Cell Line: Expression of Antibodies with Altered Glycoforms Leads to an Increase in Adcc through Higher Affinity for Fc Gamma Riii. Biotechnology and Bioengineering 74, 288-294.

Deisenhofer, J., 1981. Crystallographic Refinement and Atomic Models of a Human Fc Fragment and Its Complex with Fragment B of Protein a from Staphylococcus Aureus at 2.9- and 2.8-.Ang. Resolution. Biochemistry 20, 2361-2370.

Hodoniczky, J., Zheng, Y. Z., James, D. C., 2005. Control of Recombinant Monoclonal Antibody Effector Functions by Fc N-Glycan Remodeling in Vitro. Biotechnol Prog 21, 1644-1652.

Houde, D., Peng, Y., Berkowitz, S. A., Engen, J. R., 2010. Post-Translational Modifications Differentially Affect Igg1 Conformation and Receptor Binding. Molecular & Cellular Proteomics 9, 1716-1728.

Kaneko, Y., Nimmerjahn, F., Ravetch, J. V., 2006. Anti-Inflammatory Activity of Immunoglobulin G Resulting from Fc Sialylation. Science 313, 670-673.

Kumpel, B. M., Rademacher, T. W., Rook, G. A. W., Williams, P. J., Wilson, I. B. H., 1994. Galactosylation of Human Igg Monoclonal Anti-D Produced by Ebv-Transformed B-Lymphoblastoid Cell Lines Is Dependent on Culture Method and Affects Fc Receptor-Mediated Functional Activity. Human Antibodies and Hybridomas 5, 143-151.

Kumpel, B. M., Wang, Y., Griffiths, H. L., Hadley, A. G., Rook, G. A. W., 1995. The Biological Activity of Human Monoclonal Igg Anti-D Is Reduced by Beta-Galactosidase Treatment. Human Antibodies and Hybridomas 6, 82-88.

Mimura, Y., Church, S., Ghirlando, R., Ashton, P. R., Dong, S., Goodall, M., Lund, J., Jefferis, R., 2000. The Influence of Glycosylation on the Thermal Stability and Effector Function Expression of Human Igg1-Fc: Properties of a Series of Truncated Glycoforms. Molecular Immunology 37, 697-706.

Samuelsson, A., Towers, T. L., Ravetch, J. V., 2001. Anti-Inflammatory Activity of Ivig Mediated through the Inhibitory Fc Receptor. Science 291, 484-486.

Scallon, B. J., Tam, S. H., McCarthy, S. G., Cal, A. N., Raju, T. S., 2007. Higher Levels of Sialylated Fc Glycans in Immunoglobulin G Molecules Can Adversely Impact Functionality. Molecular Immunology 44, 1524-1534.

Shields, R. L., Lai, J., Keck, R., O'Connell, L. Y., Hong, K., Meng, Y. G., Weikert, S. H. A., Presta, L. G., 2002. Lack of Fucose on Human Igg1 N-Linked Oligosaccharide Improves Binding to Human Fc Gamma Riii and Antibody-Dependent Cellular Toxicity. Journal of Biological Chemistry 277, 26733-26740.

Stone, G. C., Sjobring, U., Bjorck, L., Sjoquist, J., Barber, C. V., Nardella, F. A., 1989. The Fc Binding Site for Streptococcal Protein G Is in the C Gamma 2-C Gamma 3 Interface Region of Igg and Is Related to the Sites That Bind Staphylococcal Protein a and Human Rheumatoid Factors. Journal of immunology (Baltimore, Md.: 1950) 143, 565-570.

Umana, P., Jean-Mairet, J., Moudry, R., Amstutz, H., Bailey, J. E., 1999. Engineered Glycoforms of an Antineuroblastoma Igg1 with Optimized Antibody-Dependent Cellular Cytotoxic Activity. Nature Biotechnology 17, 176-180.

Walker, M. R., Lund, J., Thompson, K. M., Jefferis, R., 1989. Aglycosylation of Human Igg1 and Igg3 Monoclonal-Antibodies Can Eliminate Recognition by Human-Cells Expressing Fc-Gamma-Ri and or Fc-Gamma-Rii Receptors. Biochemical Journal 259, 347-353.

Warnock, D., Bai, X. M., Autote, K., Gonzales, J., Kinealy, K., Yan, B., Oian, J., Stevenson, T., Zopf, D., Bayer, R. J., 2005. In Vitro Galactosylation of Human Igg at 1 Kg Scale Using Recombinant Galactosyltransferase. Biotechnology and Bioengineering 92, 831-842.

Wright, A., Sato, Y., Okada, T., Chang, K. H., Endo, T., Morrison, S. L., 2000. In Vivo Trafficking and Catabolism of Igg1 Antibodies with Fc Associated Carbohydrates of Differing Structure. Glycobiology 10, 1347-1355.

Although the present invention and its advantages have been described in detail, it should be understood that various changes, substitutions and alterations can be made herein without departing from the scope of the invention as defined by the appended claims. Moreover, the scope of the present application is not intended to be limited to the particular embodiments of the process, composition of matter, means, methods and steps described in the specification.

We claim:

1. A method to enzymatically alter the Fc region of a glycoform antibody comprising:
   (a) providing a sample comprising a population of individual glycoform antibodies (mAb) and non-target proteins;
   (b) loading the sample onto a solid phase support comprising affinity ligands, each respective one affinity ligand capable of binding a respective individual glycoform antibody
   (c) allowing binding of the individual glycoform antibodies to respective ones of the affinity ligands, thereby immobilizing individual antibodies on said solid phase support and exposing glycans of the Fc region wherein said affinity ligand is selected from the group consisting of Protein A, Protein G, Protein A/G, Protein L and combinations thereof;
   (d) washing said solid phase support to wash away any unbound glycoform antibodies and non-target proteins from said sample;
   (e) contacting said affinity ligand bound glycoform antibodies having exposed glycans of the Fc region with a first reaction buffer comprising one or more first enzymes to effect galactosylation, sialylation, degalactosylation, desialylation or conversion to core non-galactosylated or core mannose structures and, if required by the one or more first enzymes, one or more nucleotide sugars and/or cofactors for a time sufficient and under conditions sufficient to enzymatically modify the glycoform of the Fc region;
   (f) washing said solid phase support to wash away any reaction buffer and reaction byproducts;
   (g) contacting said affinity ligand bound glycoform antibodies having exposed glycans of the Fc region with a second reaction buffer comprising one or more second enzymes to effect galactosylation, sialylation, or conversion to core non-galactosylated or core mannose structures and, if required by the one or more second enzymes, one or more nucleotide sugars and/or cofactors for a time sufficient and under conditions sufficient to enzymatically further modify the glycoform of the Fc region; and
   (h) releasing the modified glycoform antibodies from said affinity ligand,
   wherein said glycoform antibodies comprise polyclonal antibodies, monoclonal antibodies, human monoclonal antibodies, humanized monoclonal antibodies, recombinantly produced monoclonal antibodies, single chain antibodies and any fragments of the aforementioned antibodies.

2. The method of claim 1, wherein said glycoform antibody is selected from the group consisting of cetuximab, rituximab, muromonab-CD3, abciximab, daclizumab, basiliximab, palivizumab, infliximab, trastuzumab, gemtuzumab ozogamicin, alemtuzumab, ibritumomab tiuxetan, adalimumab, omalizumab, tositumomab, 1-131 tositumomab, efalizumab, bevacizumab, panitumumab, pertuzumab, natalizumab, etanercept, IGN101, volociximab, Anti-CD80 mAb, Anti-CD23 mAb, CAT-3888, CDP-791, eraptuzumab, MDX-010, MDX-060, MDX-070, matuzumab, CP-675, 206, CAL, SGN-30, zanolimumab, adecatumumab, oregovomab, nimotuzumab, ABT-874, denosumab, AM 108, AMG 714, fontolizumab, daclizumab, golimumab, CNTO 1275, ocrelizumab, belimumab, epratuzumab, MLN1202, visilizumab, tocilizumab, ocrerlizumab, certolizumab pegol, eculizumab, pexelizumab, abciximab, ranibizimumab, mepolizumab, TNX-355, and MYO-029.

3. The method of claim 2, wherein said glycoform antibody is a monoclonal antibody selected from EG2-hFc, cetuximab and aIL8-hFc; or a polyclonal antibody that is a human serum IgG.

4. The method of claim 1, wherein the modified glycoform antibody comprises the presence of galactose in the glycans of the Fc region for the treatment of a cancer, or wherein the glycoform antibody comprises the presence of terminal sialic acid in the glycans of the Fc region for the treatment of an autoimmune disorder or an inflammatory disorder.

5. The method of claim 1, wherein the glycoform modification is selected from G2 glycoform, G0 glycoform, M3 glycoform, S2 glycoform, A2B glycoform, A2BG2 glycoform and S1 glycoform.

6. The method of claim 1, wherein said one or more first enzymes are selected from the group consisting of:
   Mannosyl-glucosamine transferases selected from MGAT1, MGAT2 and MGAT3;
   Galactosyltransferases selected from β4GalT1, β4GalT2, β4GalT3, β4GalT4, β4GalT5, β4GalT6 and β4GalT7;
   Sialyltransferases selected from ST6Gall and ST6Gal2;
   Mannosidases selected from α-Mannosidase-I, α-Mannosidase-II, α(1-2)-Mannosidase, α(1-6) Mannosidase, α(1-2, 3) Mannosidase, and α(1-2, 3, 6) Mannosidase;
   Hexosaminidases selected from β-N-acetylhexosaminidase, β-N-Acetylglucosaminidase, and α-N-acetylglucosaminidase;
   Galactosidases selected from β-galactosidase, β(1-4) galactosidase and α(1-3, 6) galactosidase;
   Sialidases selected from α(2-3, 6, 8) sialidase and α(2-3) sialidase; Fucosidases selected from α-L-fucosidase, α(1-6) fucosidase, α(1-2) fucosidase, α(1-3, 4) fucosidase and α(1-2, 3, 4) fucosidase); and
any combinations of the foregoing.

7. The method of claim 1, wherein said first reaction buffer and/or said second reaction buffer are provided at a pH of about 6.0-8.0 or at a pH of about 7.2.

8. The method of claim 1, wherein said first reaction buffer and/or said second reaction buffer are provided at a temperature of about 25° C. to about 40° C. or at a temperature of about 37° C.

9. The method of claim 1, wherein the nucleotide sugars are selected from the group consisting of UDP-Glc, UDP-Gal, UDP-GalNAc, UDP-GlcNAc, UDP-GlcUA, UDP-Xyl, GDP-Man, GDP-Fuc, CMP-Neu5Ac, CMP-Neu5Gc and combinations thereof.

10. The method of claim 1, wherein the nucleotide sugars are provided in a concentration of about 0.5 to about 5 mM or about 1 to about 1.5 mM.

11. The method of claim 1, wherein the cofactor is selected from the group consisting of $Mn^{2+}$, $Ca^{2+}$, $Mg^{2+}$, $Na^+$, $K^+$, α-Lactalbumin and combinations thereof and provided in a range of from about 2 to about 10 mM.

12. The method of claim 1, wherein said affinity ligand is provided linked to a solid support selected from the group consisting of agarose, polyacrylic, polystyrene and other synthetic polymers.

13. The method of claim 1, wherein contacting said affinity ligand bound glycoform antibody with the first reaction buffer and/or the second reaction buffer is done for up to about 72 hours and wherein said releasing is done using an elution buffer.

14. The method of claim 1, wherein step (d) comprises washing using a wash buffer at pH of about 6.0-8.0 to wash the affinity ligand bound glycoform antibodies, wherein said wash buffer comprises PBS, TRIS buffer, BIS-TRIS buffer, MES buffer, BES buffer, MOPS buffer or HEPES buffer.

15. The method of claim 1, wherein said sample is provided from a cell culture supernatant, from serum or from a biological sample.

16. The method of claim 1, further comprising formulating said modified glycoform antibody into a composition for the treatment of a cancer, an autoimmune disorder or an inflammatory disorder, said composition optionally comprising one or more of a pharmaceutically acceptable carrier, a therapeutic agent, an isotonizing agent and an adjuvant.

17. A method of generating monoclonal antibodies (mAbs) having a desired glycosylation profile in the Fc region for cancer immunotherapy, said method comprising:
(a) adding a monoclonal antibody (mAb) population from a sample to a solid phase support comprising affinity ligands, each respective one affinity ligand binding an individual member of said mAb population and immobilizing the bound members of the mAb population on said solid phase support exposing glycans of the Fc region, wherein said affinity ligand is selected from the group consisting of Protein A, Protein G, Protein A/G, Protein L and combinations thereof;
(b) washing said solid phase support with a buffer to wash away any unbound members of the mAb population and non-target proteins from said sample;
(c) contacting said bound members of the mAb population immobilized on said solid phase support with a reaction buffer comprising one or more enzymes to perform desialylation of said immobilized mAb;
(d) washing said solid phase support with a buffer to wash away any reaction buffer and reaction byproducts;
(e) contacting said bound members of the mAb population immobilized on said solid phase support with a reaction buffer comprising one or more enzymes to perform galactosylation of said immobilized mAb;
(f) recovering desialylated and galactosylated glycoform mAbs for cancer immunotherapy.

18. A method of generating antibodies having a desired modified glycoform profile for immune disorder or inflammatory immunotherapy from a glycoform antibody population, said method comprising:
(a) adding said glycoform antibody population from a sample to a solid phase support comprising affinity ligands, each affinity ligand binding an individual member of the glycoform antibody population and immobilizing the bound members of the glycoform antibody population on said solid phase support and exposing glycans of the Fc region, wherein said affinity ligand is selected from the group consisting of Protein A, Protein G, Protein A/G, Protein L and combinations thereof;
(b) washing said solid phase with a buffer to wash away any unbound members of the antibody population and non-target proteins from said sample;
(c) contacting said immobilized glycoform antibodies on said solid phase support with a reaction buffer comprising one or more enzymes to perform desialylation of said immobilized antibody at the Fc region;
(d) washing said solid phase support with a buffer to wash away any reaction buffer and reaction byproducts;
(e) contacting said immobilized glycoform antibody antibodies on said solid phase support with a reaction buffer comprising one or more enzymes to perform galactosylation of said immobilized antibody at the Fc region;
(f) washing said solid phase support with a buffer to wash away any reaction buffer and reaction byproducts;
(g) contacting said immobilized glycoform antibody antibodies on said solid phase support with a reaction buffer comprising one or more enzymes to perform sialylation of said immobilized antibody at the Fc region; and
(e) recovering the modified glycoform antibodies for immune disorder or inflammatory disorder immunotherapy.

19. The method of claim 1, wherein said one or more second enzymes are independently selected from the group consisting of:
Mannosyl-glucosamine transferases selected from MGAT1, MGAT2 and MGAT3;
Galactosyltransferases selected from β4GalT1, β4GalT2, β4GalT3, β4GalT4, β4GalT5, β4GalT6 and β4GalT7;
Sialyltransferases selected from ST6Gal1 and ST6Gal2; and
any combinations of the foregoing.

* * * * *